(12) United States Patent
Antzelevitch et al.

(10) Patent No.: US 7,968,296 B2
(45) Date of Patent: Jun. 28, 2011

(54) CACNB2 NUCLEIC ACID MUTATIONS AS INDICATORS OF SHORTER THAN NORMAL QT INTERVAL AND ST SEGMENT ELEVATION ASSOCIATED WITH SUDDEN CARDIAC DEATH

(76) Inventors: Charles Antzelevitch, New Hartford, NY (US); Guido Pollevick, Dobbs Ferry, NY (US)

( * ) Notice: Subject to any disclaimer, the term of this patent is extended or adjusted under 35 U.S.C. 154(b) by 0 days.

(21) Appl. No.: 12/901,070

(22) Filed: Oct. 8, 2010

(65) Prior Publication Data
US 2011/0053165 A1    Mar. 3, 2011

Related U.S. Application Data

(62) Division of application No. 11/983,005, filed on Nov. 6, 2007, now Pat. No. 7,833,718.

(60) Provisional application No. 60/856,943, filed on Nov. 6, 2006.

(51) Int. Cl.
*C12Q 1/68*    (2006.01)
*C07H 21/00*   (2006.01)
*C07K 14/435*  (2006.01)
*C07K 14/705*  (2006.01)

(52) U.S. Cl. .................. 435/6.17; 435/91.2; 536/23.5; 536/24.31; 530/350

(58) Field of Classification Search .................. None
See application file for complete search history.

*Primary Examiner* — Christine J Saoud
*Assistant Examiner* — Jon M Lockard

(57) ABSTRACT

Previously unknown mutations of the CACNA1C and CACNB2b genes are disclosed which are involved in ion channel disruptions associated with shorter than normal QT interval and ST segment elevation syndrome. These mutations are utilized to diagnose and screen for shorter than normal QT interval and ST segment elevation syndrome, thus providing modalities for diagnosing syncope and/or sudden cardiac death and/or predicting susceptibility to syncope and/ or sudden cardiac death. Nucleic acid probes are provided which selectively hybridize to the mutant nucleic acids described herein. Antibodies are provided which selectively bind to the mutant polypeptides described herein. The mutations described herein are also utilized to screen for compounds useful in treating the symptoms manifest by such mutations.

4 Claims, 12 Drawing Sheets

MVNENTRMYIPEENHQGSNYGSPRPAHANMNANAAAGLAPEHIP
TPGAALSWQAAIDAARQAKLMGSAGNATISTVSSTQRKRQQYGKPKKQGSTTATRPPR
ALLCLTLKNPIRRACISIVEWKSFEIIILLTIFANCVALAIYIPFPEDDSNATNSNLE
RVEYLFLIIFTVEAFLKVIAYGLLFHPNAYLRNGWNLLDFIIVVVGLFSAILEQATKA
DGANALGGKGAGFDVKALRAFRVLRPLRLVSGVPSLQVVLNSIIKAMVPLLHIALLVL
FVIIIYAIIGLELFMGKMHKTCYNQEGIADVPAEDDPSPCALETGHGRQCQNGTVCKP
GWDGPKHGITNFDNFAFAMLTVFQCITMEGWTDVLYWVNDAVGRDWPWIYFVTLIIIG
SFFVLNLVLGVLSGEFSKEREKAKARGDFQKLREKQQLEEDLKGYLDWITQAEDIDPE
NEDEGMDEEKPRNMSMPTSETESVNTENVAGGDIEGENCGARLAHRISKSKFSRYWRR
WNRFCRRKCRAAVKSNVFYWLVIFLVFLNTLTIASEHYNQPNWLTEVQDTANKALLAL
FTAEMLLKMYSLGLQAYFVSLFNRFDCFVVCGGILETILVETKIMSPLGISVLRCVRL
LRIFKITRYWNSLSNLVASLLNSVRSIASLLLLLFLFIIIFSLLGMQLFGGKFNFDEM
QTRRSTFDNFPQSLLTVFQILTGEDWNSVMYDGIMAYGGPSFPGMLVCIYFIILFICG
NYILLNVFLAIAVDNLADAESLTSAQKEEEEEKERKKLARTASPEKKQELVEKPAVGE
SKEEKIELKSITADGESPPATKINMDDLQPNENEDKSPYPNPETTGEEDEEEPEMPVG
PRPRPLSELHLKEKAVPMPEASAFFIFSSNNRFRLQCHRIVNDTIFTNLILFFILLSS
ISLAAEDPVQHTSFRNHILFYFDIVFTTIFTIEIALKMTAYGAFLHKGSFCRNYFNIL
DLLVVSVSLISFGIQSSAINVVKILRVLRVLRPLRAINRAKGLKHVVQCVFVAIRTIG
NIVIVTTLLQFMFACIGVQLFKGKLYTCSDSSKQTEAECKGNYITYKDGEVDHPIIQP
RSWENSKFDFDNVLAAMMALFTVSTFEGWPELLYRSIDSHTEDKGPIYNYRVEISIFF
IIYIIIAFFMMNIFVGFVIVTFQEQGEQEYKNCELDKNQRQCVEYALKARPLRRYIP
KNQHQYKVWYVVNSTYFEYLMFVLILLNTICLAMQHYGQSCLFKIAMNILNMLFTGLF
TVEMILKLIAFKPKHYFCDAWNTFDALIVVGSIVDIAITEVNPAEHTQCSPSMNAEEN
SRISITFFRLFRVMRLVKLLSRGEGIRTLLWTFIKSFQALPYVALLIVMLFFIYAVIG
MQVFGKIALNDTTEINRNNNFQTFPQAVLLLFRCATGEAWQDIMLACMPGKKCAPESE
PSNSTEGETPCGSSFAVFYFISFYMLCAFLIINLFVAVIMDNFDYLTRDWSILGPHHL
DEFKRIWAEYDPEAKGRIKHLDVVTLLRRIQPPLGFGKLCPHRVACKRLVSMNMPLNS

FIG. 5A

DGTVMFNATLFALVRTALRIKTEGNLEQANEELRAIIKKIWKRTSMKLLDQVVPPAGD

DEVTVGKFYATFLIQEYFRKFKKRKEQGLVGKPSQRNALSLQAGLRTLHDIGPEIRRA

ISGDLTAEEELDKAMKEAVSAASEDDIFRRAGGLFGNHVSYYQSDGRSAFPQTFTTQR

PLHINKAGSSQGDTESPSHEKLVDSTFTPSSYSSTGSNANINNANNTALGRLPRPAGY

PSTVSTVEGHGPPLSPAIRVQEVAWKLSSNRCHSRESQAAMAGQEETSQDETYEVKMN

HDTEACSEPSLLSTEMLSYQDDENRQLTLPEEDKRDIRQSPKRGFLRSASLGRRASFH

LECLKRQKDRGGDISQKTVLPLHLVHHQALAVAGLSPLLQRSHSPASFPRPFATPPAT

PGSRGWPPQPVPTLRLEGVESSEKLNSSFPSIHCGSWAETTPGGGGSSAARRVRPVSL

MVPSQAGAPGRQFHGSASSLVEAVLISEGLGQFAQDPKFIEVTTQELADACDMTIEEM

ESAADNILSGGAPQSPNGALLPFVNCRDAGQDRAGGEEDAGCVRARGRPSEEELQDSR

VYVSSL

FIG. 5B

MLDRRLIAPQTKYIIPGGSADSYTSRPSDSDVSLEEDREAVRRE

AERQAQAQLEKAKTKPVAFAVRTNVSYSAAHEDDVPVPGMAISFEAKDFLHVKEKFNN

DWWIGRLVKEGCEIGFIPSPVKLENMRLQHEQRAKQGKFYSSKSGGNSSSSLGDIVPS

SRKSTPPSSAIDIDATGLDAEENDIPANHRSPKPSANSVTSPHSKEKRMPFFKKTEHT

PPYDVVPSMRPVVLVGPSLKGYEVTDMMQKALFDFLKHRFEGRISITRVTADISLAKR

SVLNNPSKHAIIERSNTRSSLAEVQSEIERIFELARTLQLVVLDADTINHPAQLSKTS

LAPIIVYVKISSPKVLQRLIKSRGKSQAKHLNVQMVAADKLAQCPPELFDVILDENQL

EDACEHLADYLEAYWKATHPPSSSLPNPLLSRTLATSSLPLSPTLASNSQGSQGDQRT

DRSAPIRSASQAEEEPSVEPVKKSQHRSSSSAPHHNHRSGTSRGLSRQETFDSETQES

RDSAYVEPKEDYSHDHVDHYASHRDHNHRDETHGSSDHRHRESRHRSRDVDREQDHNE

CNKQRSRHKSKDRYCEKDGEVISKKRNEAGEWNRDVYIPQ

FIG. 6

ATGGTCAATGAGAATACGAGGATGTACATTCCAGA
GGAAAACCACCAAG

GTTCCAACTATGGGAGCCCACGCCCCGCCCATGCCAACATGAATGCCAAT
GCGGCAGCGGGGCTGGCCCCTGAGCACATCCCCACCCCGGGGCTGCCCT
GTCGTGGCAGGCGGCCATCGACGCAGCCCGGCAGGCTAAGCTGATGGGCA
GCGCTGGCAATGCGACCATCTCCACAGTCAGCTCCACGCAGCGGAAGCGG
CAGCAATATGGGAAACCCAAGAAGCAGGGCAGCACCACGGCCACACGCCC
GCCCCGAGCCCTGCTCTGCCTGACCCTGAAGAACCCCATCCGGAGGGCCT
GCATCAGCATTGTCGAATGGAAAT

CATTTGAAATAATTATTTTACTGACTATTTTTGCCAATTGTGTGGCCTTA
GCGATCTATATTCCCTTTCCAGAAGATGATTCCAACGCCACCAATTCCAA
CCTG

GAACGAGTGGAATATCTCTTTCTCATAATTTTTACGGTGGAAGCGTTTTT
AAAAGTAATCGCCTATGGACTCCTCTTTCACCCCAATGCCTACCTCCGCA
ACGGCTGGAACCTACTAGATTTTATAATTGTGGTTGTGGG

GCTTTTTAGTGCAATTTTAGAACAAGCAACCAAAGCAGATGGGGCAAACG
CTCTCGGAGGGAAAGGGGCCGGATTTGATGTGAAGGCGCTGAGGGCCTTC
CGCGTGCTGCGCCCCCTGCGGCTGGTGTCCGGAGTCCCAA

GTCTCCAGGTGGTCCTGAATTCCATCATCAAGGCCATGGTCCCCCTGCTG
CACATCGCCCTGCTTGTGCTGTTTGTCATCATCATCTACGCCATCATCGG
CTTGGAGCTCTTCATGGGGAAGATGCACAAGACCTGCTACAACCAGGAGG
GCATAGCAG

ATGTTCCAGCAGAAGATGACCCTTCCCCTTGTGCGCTGGAAACGGGCCAC
GGGCGGCAGTGCCAGAACGGCACGGTGTGCAAGCCCGGCTGGGATGGTCC
CAAGCACGGCATCACCAACTTTGACAACTTTGCCTTCGCCATGCTCACGG
TGTTCCAGTGCATCACCATGGAGGGCTGGACGGACGTGCTGTACTGG

GTCAATGATGCCGTAGGAAGGGACTGGCCCTGGATCTATTTTGTTACACT
AATCATCATAGGGTCATTTTTTGTACTTAACTTGGTTCTCGGTGTGCTTA
GCGG

AGAGTTTTCCAAAGAGAGGGAGAAGGCCAAGGCCCGGGGAGATTTCCAGA
AGCTGCGGGAGAAGCAGCAGCTAGAAGAGGATCTCAAAGGCTACCTGGAT
TGGATCACTCAGGCCGAAGACATCGATCCTGAGAATGAGGACGAAGGCAT
GGATGAGGAGAAGCCCCGAAACA

TGAGCATGCCCACCAGTGAGACCGAGTCCGTCAACACCGAAAACGTGGCT
GGAGGTGACATCGAGGGAGAAAACTGCGGGGCCAGGCTGGC

CCACCGGATCTCCAAGTCAAAGTTCAG

CCGCTACTGGCGCCGGTGGAATCGGTTCTGCAGAAGGAAGTGCCGCGCCG
CAGTCAAGTCTAATGTCTTCTACTGGCTGGTGATTTTCCTGGTGTTCCTC
AACACGCTCACCATTGCCTCTGAGCACTACAACCAGCCCAACTGGCTCAC
AGAAGTCCAAG

FIG. 7A (CACNA1C exons)

ACACGGCAAACAAGGCCCTGCTGGCCCTGTTCACGGCAGAGATGCTCCTG
AAGATGTACAGCCTGGGCCTGCAGGCCTACTTCGTGTCCCTCTTCAACCG
CTTTGACTGCTTCGTCGTGTGTGGCGGCATCCTGGAGACCATCCTGGTGG
AGACCAAGATCATGTCCCCACTGGGCATCTCCGTGCTCAGATGCGTCCGG
CTGCTGAGGATTTTCAAGATCACGAG

GTACTGGAACTCCTTGAGCAACCTGGTGGCATCCTTGCTGAACTCTGTGC
GCTCCATCGCCTCCCTGCTCCTTCTCCTCTTCCTCTTCATCATCATCTTC
TCCCTCCTGGGGATGCAGCTCTTTGGAGGAAAGTTCAACTTTGATGAGAT
GCAGACCCGGAGGAGCACATTCGATAACTTCCCCCAGTCCCTCCTCACTG
TGTTTCAG

ATCCTGACCGGGGAGGACTGGAATTCGGTGATGTATGATGGGATCATGGC
TTATGGCGGCCCCTCTTTTCCAGGGATGTTAGTCTGTATTTACTTCATCA
TCCTCTTCATCTGTGGAAACT

ATATCCTACTGAATGTGTTCTTGGCCATTGCTGTGGACAACCTGGCTGAT
GCTGAGAGCCTCACATCTGCCCAAAAGGAGGAGGAAGAGGAGAAGGAGAG
AAAGAAGCTGGCCAG

GACTGCCAGCCCAGAGAAGAAACAAGAGTTGGTGGAGAAGCCGGCAGTGG
GGGAATCCAAGGAGGAGAAGATTGAGCTGAAATCCATCACGGCTGACGGA
GAGTCTCCACCCGCCACCAAG

ATCAACATGGATGACCTCCAGCCCAATGAAAATGAGGATAAGAGCCCCTA
CCCCAACCCAGAAACTACAG

GAGAAGAGGATGAGGAGGAGCCAGAGATGCCTGTCGGCCCTCGCCCACGA
CCACTCTCTGAGCTTCACCTTAAGGAAAAGGCAGTGCCCATGCCAGAAGC
CAGCGCGTTTTTCATCTTCAGCTCTAACAACAG

GTTTCGCCTCCAGTGCCACCGCATTGTCAATGACACGATCTTCACCAACC
TGATCCTCTTCTTCATTCTGCTCAGCAGCATTTCCCTGGCTGCTGAGGAC
CCGGTCCAGCACACCTCCTTCAGGAACCAT

ATTCTGTTTTATTTTGATATTGTTTTACCACCATTTTCACCATTGAAAT
TGCTCTGAAG

ATGACTGCTTATGGGGCTTTCTTGCACAAGGGTTCTTTCTGCCGGAACTA
CTTCAACATCCTGGACCTGCTGGTGGTCAGCGTGTCCCTCATCTCCTTTG
GCATCCA

GTCCAGTGCAATCAATGTCGTGAAGATCTTGCGAGTCCTGCGAGTACTCA
GGCCCCTGAGGGCCATCAACAGGGCCAAGGGGCTAAAG

CATGTGGTTCAGTGTGTGTTTGTCGCCATCCGGACCATCGGGAACATCGT
GATTGTCACCACCCTGCTGCAGTTCATGTTTGCCTGCATCGGGGTCCAGC
TCTTCAAG

GGAAAGCTGTACACCTGTTCAGACAGTTCCAAGCAGACAGAGGCGGAATG
CAA

FIG. 7B (CACNA1C exons)

```
GGGCAACTACATCACGTACAAAGACGGGGAGGTTGACCACCCCATCATCC
AACCCCGCAGCTGGGAGAACAGCAAGTTTGACTTTGACAATGTTCTGGCA
GCCATGATGGCCCTCTTCACCGTCTCCACCTTCGAAGGGTGGCCAGA

GCTGCTGTACCGCTCCATCGACTCCCACACGGAAGACAAGGGCCCCATCT
ACAACTACCGTGTGGAGATCTCCATCTTCTTCATCATCTACATCATCATC
ATCGCCTTCTTCATGATGAACATCTTCGTGGGCTTCGTCATCGTCACCTT
TCAGGAGCAGGGGGAGCAGGAGTACAAGAACTGTGAGCTGGACAAGAACC
AG

CGACAGTGCGTGGAATACGCCCTCAAGGCCCGGCCCCTGCGGAGGTACAT
CCCCAAGAACCAGCACCAGTACAAAGTGTGGTACGTGGTCAACTCCACCT
ACTTCGAGTACCTGATGTTCGTCCTCATCCTGCTCAACACCATCTGCCTG
GCCATGCAG

CACTACGGCCAGAGCTGCCTGTTCAAAATCGCCATGAACATCCTCAACAT
GCTCTTCACTGGCCTCTTCACCGTGGAGATGATCCTGAAGCTCATTGCCT
TCAAACCCAAG

CACTATTTCTGTGATGCATGGAATACATTTGACGCCTTGATTGTTGTGGG
TAGCATTGTTGATATAGCAATCACCGAGGTAAAC

CCAGCTGAACATACCCAATGCTCTCCCTCTATG

AACGCAGAGGAAAACTCCCGCATCTCCATCACCTTCTTCCGCCTGTTCCG
GGTCATGCGTCTGGTGAAGCTGCTGAGCCGTGGGGAGGGCATCCGGACGC
TGCTGTGGACCTTCATCAAGTCCTTCCAG

GCCCTGCCCTATGTGGCCCTCCTGATCGTGATGCTGTTCTTCATCTACGC
GGTGATCGGGATGCAG

GTGTTTGGGAAAATTGCCCTGAATGATACCACAGAGATCAACCGGAACAA
CAACTTTCAGACCTTCCCCCAGGCCGTGCTGCTCCTCTTCAG

GTGTGCCACCGGGGAGGCCTGGCAGGACATCATGCTGGCCTGCATGCCAG
GCAAGAAGTGTGCCCCAGAGTCCGAGCCCAGCAACAGCACGGAGGGTGAA
ACACCCTGTGGTAGCAGCTTTGCTGTCTTCTACTTCATCAGCTTCTACAT
GCTCTGTGCCTTCCTG

ATCATCAACCTCTTTGTAGCTGTCATCATGGACAACTTTGACTACCTGAC
AAGGGACTGGTCCATCCTTGGTCCCCACCACCTGGATGAGTTTAAAAGAA
TCTGGGCAGAGTATGACCCTGAAGCCAA

GGGTCGTATCAAACACCTGGATGTGGTGACCCTCCTCCGGCGGATTCAGC
CGCCACTAGGTTTTGGGAAGCTGTGCCCTCACCGCGTGGCTTGCAAA

CGCCTGGTCTCCATGAACATGCCTCTGAACAGCGACGGGACAGTCATGTT
CAATGCCACCCTGTTTGCCCTGGTCAGGACGGCCCTGAGGATCAAAACAG
AAG

GGAACCTAGAACAAGCCAATGAGGAGCTGCGGGCGATCATCAAGAAGATC
TGGAAGCGGACCAGCATGAAGCTGCTGGACCAGGTGGTGCCCCCTGCAGG
TG
```

FIG. 7C  *(CACNA1C exons)*

ATGATGAGGTCACCGTTGGCAAGTTCTACGCCACGTTCCTGATCCAGGAG
TACTTCCGGAAGTTCAAGAAGCGCAAAGAGCAGGGCCTTGTGGGCAAGCC
CTCCCAGAGGAACGCGCTGTCTCTGCAG

GCTGGCTTGCGCACACTGCATGACATCGGGCCTGAGATCCGACGGGCCAT
CTCTGGAGATCTCACCGCTGAGGAGGAGCTGGACAAGGCCATGAAGGAGG
CTGTGTCCGCTGCTTCTGAAGATGACATCTTCAGG

AGGGCCGGTGGCCTGTTCGGCAACCACGTCAGCTACTACCAAAGCGACGG
CCGGAGCGCCTTCCCCCAGACCTTCACCACTCAGCGCCCGCTGCACATCA
ACAAGGCGGGCAGCAGCCAGGGCGACACTGAGTCGCCATCCCACGAGAAG
CTGGTGGACTCCACCTTCACCCCGAGCAGCTACTCGTCCACCGGCTCCAA
CGCCAACATCAACAACGCCAACAACACCGCCCTGGGTCGCCTCCCTCGCC
CCGCCGGCTACCCCAGCACGGTCAGCACTGTGGAGGGCCACGGGCCCCCC
TTGTCCCCTGCCATCCGGGTGCAGGAGGTGGCGTGGAAGCTCAGCTCCAA
CAG

GTGCCACTCCCGGGAGAGCCAGGCAGCCATGGCGGGTCAGGAGGAGACGT
CTCAGGATGAGACCTATGAAGTGAAGATGAACCATGACACGGAGGCCTGC
AGTGAGCCCAGCCTGCTCTCCACAGAGAT

GCTCTCCTACCAGGATGACGAAAATCGGCAACTGACGCTCCCAGAGGAGG
ACAAGAGGGACATCCGGCAATCTCCGAAGAGGGGTTTCCTCCGCTCTGCC
TCACTAG

GTCGAAGGGCCTCCTTCCACCTGGAATGTCTGAAGCGACAGAAGGACCGA
GGGGGAGACATCTCTCAGAAGACAGTCCTGCCCTTGCATCTGGTTCATCA
TCAG

GCATTGGCAGTGGCAGGCCTGAGCCCCCTCCTCCAGAGAAGCCATTCCCC
TGCCTCATTCCCTAGGCCTTTTGCCACCCCACCAGCCACACCTGGCAGCC
GAGGCTGGCCCCACAGCCCGTCCCCACCCTGCGGCTTGAGGGGGTCGAG
TCCAGTGAGAAACTCAACAGCAGCTTCCCATCCATCCACTGCGGCTCCTG
GGCTGAGACCACCCCGGTGGCGGGGCAGCAGCGCCGCCGGAGAGTCC
GGCCCGTCTCCCTCATGGTGCCCAGCCAGGCTGGGGCCCCAGGGAGGCAG
TTCCACGGCAGTGCCAGCAGCCTGGTGGAAGCG

GTCTTGATTTCAGAAGGACTGGGGCAGTTTGCTCAAGATCCCAAGTTCAT
CGAGGTCACCACCCAGGAGCTGGCCGACGCCTGCGACATGACCATAGAGG
AGATGGAGAGCGCGGCCGACAACATCCTCAGCGGGGGCGCCCCACAGAGC
CCCAATGGCGCCCTCTTACCCTTTGTGAACTGCAGGGACGCGGGGCAGGA
CCGAGCCGGGGGCGAAGAGGACGCGGGCTGTGTGCGCGCGCGGGTCGAC
CGAGTGAGGAGGAGCTCCAGGACAGCAGGGTCTACGTCAGCAGCCTGTAG

FIG. 7D
*(CACNA1C exons)*

CACNB2b RNA:

```
ATGCTTGACA GACGCCTTAT AGCTCCTCAA ACTAAATACA TTATTCCTGG
GGGTTCGGCA GACTCCTACA CTAGCCGTCC ATCCGATTCC GATGTATCTC
TGGAGGAGGA CCGGGAGGCA GTGCGCAGAG AAGCGGAGCG GCAGGCCCAG
GCACAGTTGG AAAAAGCAAA GACAAAGCCC GTTGCATTTG CGGTTCGGAC
AAATGTCAGC TACAGTGCGG CCCATGAAGA TGATGTTCCA GTGCCTGGCA
TGGCCATCTC ATTCGAAGCA AAAGATTTTC TGCATGTTAA GGAAAAATTT
AACAATGACT GGTGGATAGG GCGATTGGTA AAGAAGGCT GTGAAATCGG
ATTCATTCCA AGCCCAGTCA AACTAGAAAA CATGAGGCTG CAGCATGAAC
AGAGAGCCAA GCAAGGGAAA TTCTACTCCA GTAAATCAGG AGGAAATTCA
TCATCCAGTT TGGGTGACAT AGTACCTAGT TCCAGAAAAT CAACACCTCC
ATCATCTGCT ATAGACATAG ATGCTACTGG CTTAGATGCA GAAGAAAATG
ATATTCCAGC AAACCACCGC TCCCCTAAAC CCAGTGCAAA CAGTGTAACG
TCACCCCACT CCAAAGAGAA AAGAATGCCC TTCTTTAAGA AGACAGAGCA
CACTCCTCCG TATGATGTGG TACCTTCCAT GCGACCAGTG GTCCTAGTGG
GCCCTTCTCT GAAGGGCTAC GAGGTCACAG ATATGATGCA AAAAGCGCTG
TTTGATTTTT TAAAACACAG ATTTGAAGGG CGGATATCCA TCACAAGGGT
CACCGCTGAC ATCTCGCTTG CCAAACGCTC GGTATTAAAC AATCCCAGTA
AGCACGCAAT AATAGAAAGA TCCAACACAA GGTCAAGCTT AGCGGAAGTT
CAGAGTGAAA TCGAAGGAT TTTTGAACTT GCAAGAACAT TGCAGTTGGT
GGTCCTTGAC GCGGATACAA TTAATCATCC AGCTCAACTC AGTAAAACCT
CCTTGGCCCC TATTATAGTA TATGTAAAGA TTTCTTCTCC TAAGGTTTTA
CAAAGGTTAA TAAAATCTCG AGGGAAATCT CAAGCTAAAC ACCTCAACGT
CCAGATGGTA GCAGCTGATA AACTGGCTCA GTGTCCTCCA GAGCTGTTCG
ATGTGATCTT GGATGAGAAC CAGCTTGAGG ATGCCTGTGA GCACCTTGCC
GACTATCTGG AGGCCTACTG GAAGGCCACC ATCCTCCCA GCAGTAGCCT
CCCCAACCCT CTCCTTAGCC GTACATTAGC CACTTCAAGT CTGCCTCTTA
GCCCCACCCT AGCCTCTAAT TCACAGGGTT CTCAAGGTGA TCAGAGGACT
GATCGCTCCG CTCCTATCCG TTCTGCTTCC CAAGCTGAAG AAGAACCTAG
TGTGGAACCA GTCAAGAAAT CCCAGCACCG CTCTTCCTCC TCAGCCCCAC
ACCACAACCA TCGCAGTGGG ACAAGTCGCG GCCTCTCCAG GCAAGAGACA
TTTGACTCGG AAACCCAGGA GAGTCGAGAC TCTGCCTACG TAGAGCCAAA
GGAAGATTAT TCCCATGACC ACGTGGACCA CTATGCCTCA CACCGTGACC
ACAACCACAG AGACGAGACC CACGGGAGCA GTGACCACAG ACACAGGGAG
TCCCGGCACC GTTCCCGGGA CGTGGATCGA GAGCAGGACC ACAACGAGTG
CAACAAGCAG CGCAGCCGTC ATAAATCCAA GGATCGCTAC TGTGAAAAGG
ATGGAGAAGT GATATCAAAA AAACGGAATG AGGCTGGGGA GTGGAACAGG
GATGTTTACA TCCCCCAATG A
```

FIG. 8

CACNB2 NUCLEIC ACID MUTATIONS AS INDICATORS OF SHORTER THAN NORMAL QT INTERVAL AND ST SEGMENT ELEVATION ASSOCIATED WITH SUDDEN CARDIAC DEATH

CROSS-REFERENCE TO RELATED APPLICATION

This application is a Divisional Application which claims the benefit of and priority to U.S. patent application Ser. No. 11/983,005, filed Nov. 6, 2007, which claims priority from U.S. Provisional Application No. 60/856,943, filed on Nov. 6, 2006, the entire contents of which are both hereby incorporated by reference in their entireties.

BACKGROUND

1. Technical Field

The invention relates to diagnosis of sudden cardiac death or potential for syncope or sudden cardiac death in patients who have mutations in calcium ion channel polypeptides involved in electrophysiology of the heart.

2. Background of Related Art

Cardiac arrhythmias are responsible for an estimated one million cases of syncope and sudden cardiac death among Europeans and Americans each year. Sudden cardiac death takes the lives of over 300,000 Americans annually. Cardiac arrhythmias can be acquired as a consequence of coronary heart disease or may be secondary to familial or inherited syndromes. Recent years have witnessed major strides in the understanding of sudden cardiac death in individuals with structurally normal hearts. Malignant ventricular arrhythmias account for a subgroup of these sudden deaths. There has been an explosion of information linking cardiac ion channel mutations with a wide variety of inherited arrhythmia syndromes. Idiopathic, sudden cardiac death syndromes for which there was previously no explanation are gradually coming into focus as forms of inherited ion channelopathies.

The QT interval is the surrogate electrocardiographic index of ventricular repolarization and its duration under normal conditions is mainly determined by expression, properties, and balance of the repolarizing inward sodium and calcium and outward potassium and chloride currents. Ion channels proteins are responsible for the currents that comprise the cardiac action potential and alterations in ion channel function are known to be associated with a wide spectrum of phenotypes. Long QT syndrome (LQTS) is characterized by the appearance of a long QT interval in the electrocardiogram, and an atypical polymorphic ventricular tachycardia known as torsade de pointes, and a high risk of sudden cardiac death. Congenital LQT syndrome is an inherited condition of abnormal cardiac repolarization. Acquired LQT syndrome is similar to congenital LQT syndrome but can be caused by exposure to drugs, trauma or other environmental factors. The LQTS has been associated with 10 different genes, due in large part to the pioneering studies of Keating and co-workers. The LQT8 form of LQTS, also known as Timothy syndrome, is associated with gain of function mutations in cardiac calcium channel activity. The cardiac L-type calcium channel is a protein complex formed by at least three subunits, $\alpha_1$, $\beta$ and $\alpha_2\delta$. The pore-forming $Ca_v1.2$ $\alpha_1$ subunit FIG. 5AB (SEQ. ID. NO. 1) is encoded by CACNA1C. The $\beta$ or $Ca_v\beta_{2b}$ subunit FIG. 6 (SEQ. ID. NO. 2), encoded by CACNB2b, modulates calcium channel activity in the human heart and enables trafficking by suppressing an endoplasmic reticulum retention signal in the I-II loop of the $\alpha_1$ subunit. A gain of function in calcium channel current secondary to mutations in CACNA1C has been shown to produce a sudden death syndrome associated with a prolongation of the QT interval. See, e.g., Splawski et al., *Cell*. (2004) 119:19-31 and Splawski et al., *Proc Natl Acad Sci USA*. (2005) 102:8089-8096.

Gain of function in SCN5A, the gene that encodes for the $\alpha$ subunit of the cardiac sodium channel, is associated with the LQT3 form of the Long QT syndrome (See, e.g., U.S. Pat. No. 5,599,673), while a decrease in function of the same channel is associated with Brugada syndrome and familial conduction disease. Likewise, loss of function in $I_{Ks}$ and $I_{Kr}$ is linked to other forms of Long QT, while an increase in $I_{Ks}$ current, caused by a mutation in the $\alpha$ subunit KCNQ1 (also referred to as KvLQT1), is linked to familial atrial fibrillation. The final common pathway is similar, involving alteration of ion channel activity, leading to the development of an arrhythmogenic substrate.

U.S. Pat. Nos. 6,582,913, 6,451,534, 6,432,644 and 6,277,978 are directed to screening and/or diagnosis of Long QT syndrome by analyzing the DNA sequence of the KvLQT1 or KCNE1 genes and molecular variants of these genes which cause or are involved in the pathogenesis of Long QT syndrome. U.S. Pat. Nos. 6,420,124 and 6,274,332 are directed to screening for drugs useful in treating a person having certain mutations in the KvLQT1 or KCNE1 genes. U.S. Pat. No. 6,458,542 is directed to a method for screening for susceptibility to drug induced cardiac arrhythmia by detecting a polymorphism in the KCNE1 gene. Certain mutations in the HERG (also known as KCNH2) gene have also been linked to LQT syndrome. See, e.g., U.S. Pat. No. 6,207,383.

Brugada syndrome is associated with sudden cardiac death and ventricular arrhythmia and may occur in the structurally normal heart. It is characterized by ST segment elevation in the right precordial leads (V1 to V3) and right bundle branch block. The age of onset of clinical manifestations, which can include syncope or cardiac arrest, is typically in the third or fourth decade of life. Cardiac events may occur during sleep or at rest. A loss of ion channel function in Brugada syndrome has been associated with certain mutations of the SCN5A gene.

Progressive cardiac conduction defect, also known as progressive conduction disease or Lenegre disease is another electrophysiological cardiac syndrome that is considered one of the most common. It is characterized by a progressive alteration of cardiac conduction through the atrioventricular node, His-Purkinje system with left or right bundle block, which may cause syncope or sudden death. Scott et al., Nat. Genet., (1998) 23:20-21, indicate that certain mutations in SCN5A are associated with progressive conduction disease.

Short QT syndrome (SQTS) is a relatively new clinical entity originally described in 2000. Short QT syndrome is characterized by the presence of a very short QT interval in the electrocardiogram (Bazzett-corrected QT interval (QTc) of ≦330 msec), episodes of paroxysmal atrial fibrillation, ventricular arrhythmias and possible sudden death in patients with structurally normal hearts. An autosomal dominant pattern of transmission with a high incidence of sudden death over several generations has been reported. SQTS has been associated with a gain of function in three distinct potassium channels (KCNH2, KCNQ1, and KCNJ2) leading to abbreviation of the electrocardiographic (ECG) QT interval and the development of malignant arrhythmias. See, e.g., application Ser. No. 10/924,375 (Pub. No. 20050130190) and Priori, et al., *Circ. Res*. (2005) 96:800-807. Loss of function mutations in SCN5A, the gene that encodes the $\alpha$-subunit of the cardiac sodium channel, have been linked to Brugada syndrome, which is characterized by an ST segment elevation in the right precordial leads (V1-V3) of the ECG and the development of polymorphic ventricular tachycardia (VT) that can result in sudden cardiac death.

Arrhythmogenesis in both Brugada and short QT syndromes may be due to amplification of heterogeneities in action potential characteristics among the different transmural cell types. See, Fish J M, Antzelevitch C., *Heart Rhythm*. 2004; 1:210-217. In Brugada syndrome, a decrease in $I_{Na}$ or $I_{Ca}$ or augmentation of any one of a number of outward currents including $I_{Kr}$, $I_{Ks}$, $I_{Cl}(Ca)$ or $I_{to}$ can cause preferential abbreviation of the right ventricular epicardial action potential, leading to the development of spatial dispersion of repolarization and thus the substrate and trigger for VT, which is usually polymorphic and less frequently monomorphic. See, Antzelevitch C, et al., *Circulation*. 2005; 111:659-670. In the short QT syndromes, preferential abbreviation of either the epicardial or endocardial response amplifies spatial dispersion of repolarization and creates the substrate for reentrant arrhythmias. See, Extramiana F, Antzelevitch C., *Circulation*. 2004; 110:3661-3666. An increase in outward current (see Brugada et al., *Circulation*. 2004; 109:30-35; Bellocq et al., *Circulation*. 2004; 109:2394-2397; Priori et al., *Circ Res*. 2005; 96:800-807) or a decrease in inward current, including calcium current, may be responsible.

There is a need to determine the underlying cause of sudden cardiac death so that diagnostic procedures can be implemented to take precautions in susceptible individuals and to aid in determinations of mortality risk.

SUMMARY

The genetic basis for a new clinical entity, characterized by syncope and/or sudden death and short QT intervals in the electrocardiogram is identified. Missense mutations in CACNA1C are associated with amino acid changes A39V and G490R and in CACNB2 for S481L encoding the $\alpha_1$ and $\beta_{2b}$ subunits of the L-type calcium channel.

In accordance with the present invention, the above-identified mutations are utilized to diagnose and screen for sudden cardiac death or to determine susceptibility to syncope and/or cardiac death. Nucleic acid probes are provided which selectively hybridize to the mutant nucleic acids described herein. Antibodies are provided which selectively bind to the mutant polypeptides described herein. The above-identified mutations are also utilized to screen for drugs useful in treating the symptoms manifest by such mutations.

BRIEF DESCRIPTION OF THE DRAWINGS

FIGS. 5A and 5B depict the amino acid sequence of a wild-type CACNA1C polypeptide (SEQ. ID. NO: 1).

FIG. 6 depicts the amino acid sequence of a wild type CACNB2b polypeptide (SEQ. ID. NO: 2).

FIGS. 7A-7D depict the exon sequences of CACNA1C (SEQ. ID. NO. 6).

FIG. 8 depicts the mRNA sequence of CACNB2b (SEQ. ID. NO. 7).

DETAILED DESCRIPTION OF PREFERRED EMBODIMENTS

Figure 1:
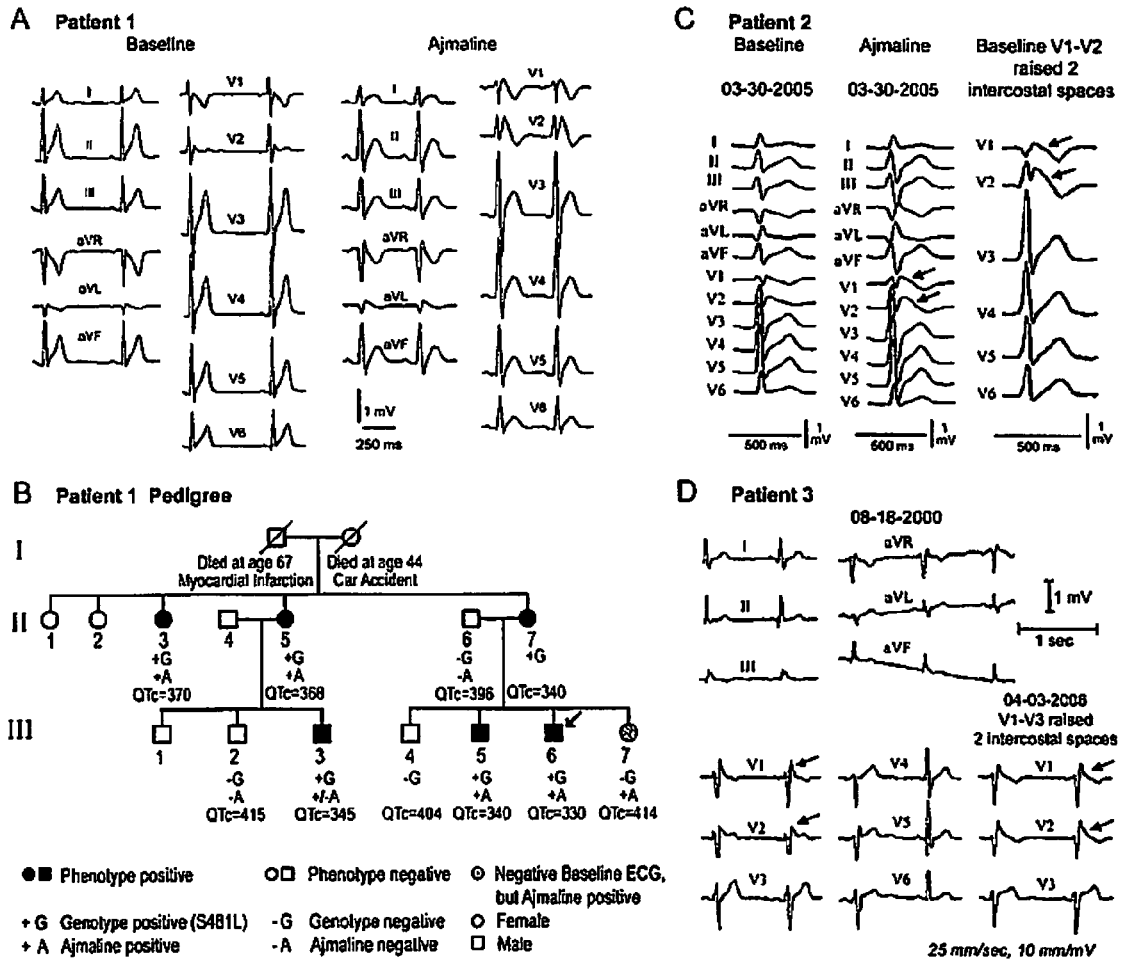
FIG. 1A depicts a series of 12 lead ECGs of patient 1 before and after ajmaline recorded with V1 and V2 displaced superiorly 2 intercostal spaces.
FIG. 1B is a schematic pedigree of family of patient 1 (III-6, arrow: proband). Arrows in ECGs depict prominent (Type I) ST segment elevation.
FIG. 1C depicts a series of 12 lead ECGs of patient 2 before and after ajmaline (1 mg/kg) or and at baseline with V1 and V2 displaced superiorly 2 intercostal spaces to unmask a type 1 ST segment elevation.
FIG. 1D depicts a series of 12 lead ECGs of patient 3 with V1-V3 in normal position and displaced superiorly 2 intercostal spaces.

In accordance with the present invention, previously unknown mutations of genes and their corresponding polypeptides are disclosed which are involved with ion channels associated with arrhythmias, syncope and/or sudden cardiac death. Described herein is a new clinical entity consisting of an ST segment elevation in the right precordial ECG leads, a shorter than normal QT interval and a history of sudden cardiac death (SCD).

Although the Brugada syndrome has thus far been linked to mutations that impede sodium channel expression or function, experimental studies have shown that the electrocardiographic and arrhythmic manifestations of the disease phenotype can be recapitulated in the coronary—perfused canine right ventricular wedge preparation using calcium channel blockers (see, Fish J M, Antzelevitch C., *Heart Rhythm*. 2004; 1:210-217), pointing to genes encoding the various subunits of the calcium channel as candidates to explain the disease phenotype. Moreover, calcium channel blockers have been reported to produce an acquired form of the Brugada syndrome in humans. See, Shimizu W., *J Electrocardiol*. 2005; 38 Suppl:22-25. Consistent with these findings, the present invention demonstrates an association between loss of function mutations in the $\alpha_1$ and $\beta_{2b}$ subunits of the cardiac L-type calcium channel and the Brugada syndrome phenotype. As used herein, the non-italics "CACNA1C" is used to designate the "$Ca_v1.2\alpha_1$ subunit" and is interchangeable with the "$Ca_v1.2\alpha_1$ subunit", and the non-italics "CACNB2" is used to designate the "$Ca_v\beta_{2b}$ subunit" and is interchangeable with the "$Ca_v\beta_{2b}$ subunit".

Evidence in support of the mutations in CACNA1C or CACNB2b as causal include the findings that: 1) mutations in two different subunits of the calcium channel are associated with similar disease phenotypes in probands with a family history of sudden cardiac death; 2) heterologous expression of mutant channels in CHO cells leads to a major loss of function consistent with the Brugada syndrome phenotype as well as with a shorter than normal QT interval; 3) the three mutations are not observed in ethnically matched healthy individuals; and 4) there is a clear genotype-phenotype correlation.

In one aspect, the invention relates to the identification of a molecular basis of shorter than normal QT interval and ST segment elevation syndrome. More specifically, missense mutations in CACNA1C are associated with amino acid changes A39V and G490R and in CACNB2 for S481L encoding the $\alpha_1$ and $\beta_{2b}$ subunits of the L-type calcium channel. Although arrhythmic diseases have previously been linked to gain of function in calcium channel current secondary to mutations in CACNA1C to produce a sudden death syndrome associated with a prolongation of the QT interval, no disease had previously been associated with a loss of function in calcium channel activity secondary to mutations in CACNA1C or CACNB2b. These mutations can contribute to syncope or a sudden death syndrome by causing a shorter than normal QT interval and ST segment elevation (Brugada syndrome phenotype).

Analysis of the mutated A39V and G490R CACNA1C gene and/or mutated S481L CACNB2b gene provides an early diagnosis of subjects with shorter than normal QT interval and ST segment elevation. Diagnostic methods include analyzing the nucleic acid sequence of each or both of the CACNA1C or CACNB2b genes of an individual to be tested and comparing them with the nucleic acid sequence of the native, nonvariant gene also known as the "wild type" (WT). Alternatively, the amino acid sequence of the respective polypeptides encoded by the CACNA1C or CACNB2b genes may be analyzed for the above-indicated mutations which respectively cause shorter than normal QT interval and ST segment elevation. Pre-symptomatic diagnosis of these syndromes will enable practitioners to treat these disorders using existing medical therapy, e.g., using an implantable cardioverter defibrillator (ICD) or agents with Class III antiarrhythmic actions (e.g., quinidine, or $I_{Kr}$ blocking agents) or via ablation techniques.

The present invention provides methods of screening the CACNA1C and/or CACNB2b genes to identify the mutations listed above. Such methods may include the step of amplifying the respective portions of the CACNA1C and/or CACNB2b genes containing and flanking the above described mutated sites, and may further include a step of providing a set of oligonucleotides which are primers for amplification of said respective portions of the CACNA1C and/or CACNB2b genes. Methods of making such primers are well within the ordinary skill in the art. The methods are useful for identifying mutations for use in either diagnosis of shorter than normal QT interval and ST segment elevation or prognosis of shorter than normal QT interval and ST segment elevation. The present invention is further directed to methods of screening humans for the presence of CACNA1C and/or CACNB2b gene variants which cause shorter than normal QT interval and ST segment elevation. Assays can be performed to screen persons for the presence of the above-described mutations in either the nucleic acid encoding the polypeptide, the polypeptide itself and/or fragments thereof. In one embodiment, the assay may be a microchip or microarray assay. The nucleic acid encoding the polypeptide and/or the polypeptide itself or a fragment thereof may also be used in assays to screen for drugs which will be useful in treating or preventing the occurrence of shorter than normal QT interval and ST segment elevation.

The present invention also provides nucleic acid probes which will respectively and selectively hybridize to nucleic acid coding for CACNA1C or CACNB2b polypeptides containing the above-described mutations, for example, the mutation which causes shorter than normal QT interval and ST segment elevation, said mutation being a substitution of alanine for valine at amino acid residue 39 of the CACNA1C polypeptide, but will not hybridize to DNA encoding wild type CACNA1C under hybridization conditions which only permit hybridization products to form which are fully complementary in the region of the mutation. For example, the present invention provides a nucleic acid probe which will hybridize, e.g., under stringent conditions, to nucleic acid coding for a mutant CACNA1C polypeptide containing a mutation which causes shorter than normal QT interval and ST segment elevation under conditions which only permit hybridization products to form which are complementary in the region causing said mutation, said mutation in said nucleic acid being a substitution of adenine for guanine at position 1468 in exon 10 of CACNA1C (coding for G490R in the polypeptide) or cytosine for thymine at nucleotide position 116 in exon 2 of CACNA1C (coding for A39V in the polypeptide), but will not hybridize to nucleic acid encoding wild type CACNA1C polypeptide. Likewise, the present invention provides a nucleic acid probe which will hybridize, e.g., under stringent conditions, to nucleic acid coding for a mutant CACNB2b polypeptide containing a mutation which causes shorter than normal QT interval and ST segment elevation under conditions which only permit hybridization products to form which are complementary in the region causing said mutation, wherein said mutation is a substitution of cytosine for thymine at position 1442 in exon 13 of CACNB2b (coding for S481L in the polypeptide). As used herein, "wild-type" or "WT" is the naturally occurring, non-mutant nucleic acid or polypeptide.

The present invention also provides a method for diagnosing a polymorphism which causes shorter than normal QT interval and ST segment elevation by hybridizing one or more such nucleic acid probes to a patient's sample of DNA or RNA under conditions which only permit hybridization products which are fully complementary in the region of the mutation to form, and determining the presence or absence of a signal indicating a hybridization product, the presence of a hybridization signal indicating the presence of shorter than normal QT interval and ST segment elevation. In one embodiment, the patient's DNA or RNA may be amplified and the amplified DNA or RNA is hybridized with said probes. The hybridization may be performed in situ. A single-stranded conformation polymorphism technique may be used to assay for any of said mutations.

The present invention also provides a method for diagnosing a polymorphism which causes shorter than normal QT interval and ST segment elevation, said polymorphism being a mutation substituting a serine at residue 481 of the CACNB2b polypeptide, said method including using a single-stranded conformation polymorphism technique to assay for said polymorphism. The present invention also provides a method for diagnosing a polymorphism which causes shorter than normal QT interval and ST segment elevation, said polymorphism being a mutation substituting a valine at residue 39 of the CACNA1C polypeptide, said method including using a single-stranded conformation polymorphism technique to assay for said polymorphism. The present invention also provides a method for diagnosing a polymorphism which causes shorter than normal QT interval and ST segment elevation, said polymorphism being a mutation substituting a glycine at residue 490 of the CACNA1C polypeptide, said method including using a single-stranded conformation polymorphism technique to assay for said polymorphism. The present invention also provides a method for diagnosing a polymorphism which causes shorter than normal QT interval and ST segment elevation, said polymorphism selected from the group consisting of a mutation substituting a serine at residue 481 of the CACNB2b polypeptide, a mutation substituting a valine at residue 39 of the CACNA1C polypeptide, a mutation substituting a glycine at residue 490 of the CACNA1C polypeptide and combinations thereof, said method including using a single-stranded conformation polymorphism technique to assay for said polymorphism.

The present invention also provides a method for diagnosing a polymorphism which causes shorter than normal QT interval and ST segment elevation comprising identifying a mismatch between a patient's DNA or RNA and a wild-type DNA or RNA probe wherein said probe hybridizes to the region of DNA or RNA encoding amino acid residue 481 of the CACNB2b polypeptide. The mismatch may be identified by an RNase assay wherein the patient's DNA or RNA, has been amplified and said amplified DNA or RNA, is hybridized with said probe. The hybridization may be performed in situ. The present invention also provides a method for diagnosing a polymorphism which causes shorter than normal QT interval and ST segment elevation comprising identifying a mismatch between a patient's DNA or RNA and a wild-type DNA or RNA probe wherein said probe hybridizes to the region of DNA or RNA encoding amino acid residue 39 of the CACNA1C polypeptide. The mismatch may be identified by an RNase assay wherein the patient's DNA or RNA, has been amplified and said amplified DNA or RNA, is hybridized with said probe. The hybridization may be performed in situ. The present invention also provides a method for diagnosing a polymorphism which causes shorter than normal QT interval and ST segment elevation comprising identifying a mismatch between a patient's DNA or RNA and a wild-type DNA or RNA probe wherein said probe hybridizes to the region of DNA or RNA encoding amino acid residue 490 of the CACNA1C polypeptide. The mismatch may be identified by an RNase assay wherein the patient's DNA or RNA, has been amplified and said amplified DNA or RNA, is hybridized with said probe. The hybridization may be performed in situ. The present invention also provides a method for diagnosing a polymorphism which causes shorter than normal QT interval and ST segment elevation comprising identifying a mismatch between a patient's DNA or RNA and a wild-type DNA or RNA probe wherein said probe hybridizes to a region of DNA or RNA, the region of DNA or RNA encoding an amino acid residue, the amino acid residue selected from the group consisting of residue 481 of the CACNB2b polypeptide, residue 39 of the CACNA1C polypeptide, residue 490 of the CACNA1C polypeptide, and combinations thereof. The mismatch may be identified by an RNase assay wherein the patient's DNA or RNA, has been amplified and said amplified DNA or RNA, is hybridized with said probe. The hybridization may be performed in situ.

Also provided is a method for diagnosing a polymorphism which causes shorter than normal QT interval and ST segment elevation which includes amplifying the region of the CACNB2b DNA or RNA surrounding and including base position 1442 in exon 13, and determining whether a C to T substitution at position 1442 exists, said alteration being indicative of shorter than normal QT interval and ST segment elevation. The present invention also provides a method for diagnosing a polymorphism which causes shorter than normal QT interval and ST segment elevation by amplifying the region of the CACNB2b DNA or RNA encoding amino acid 481 of the CACNB2b polypeptide and sequencing the amplified DNA or RNA wherein substitution of nucleic acid encoding leucine at position 481 is indicative of shorter than normal QT interval and ST segment elevation. Also provided is a method for diagnosing a polymorphism which causes shorter than normal QT interval and ST segment elevation which includes amplifying the region of the CACNA1C DNA or RNA surrounding and including base position 1468 in exon 10, and determining whether an A to G substitution at position 1468 exists, said alteration being indicative of shorter than normal QT interval and ST segment elevation. The present invention also provides a method for diagnosing a polymorphism which causes shorter than normal QT interval and ST segment elevation by amplifying the region of the CACNA1C DNA or RNA encoding amino acid 490 of the CACNA1C polypeptide and sequencing the amplified DNA or RNA wherein substitution of nucleic acid encoding arginine at position 490 is indicative of shorter than normal QT interval and ST segment elevation. Also provided is a method for diagnosing a polymorphism which causes shorter than normal QT interval and ST segment elevation which includes amplifying the region of the CACNA1C DNA or RNA surrounding and including base position 116 in exon 2, and determining whether an C to T substitution at position 116 exists, said alteration being indicative of shorter than normal QT interval and ST segment elevation. The present invention also provides a method for diagnosing a polymorphism which causes shorter than normal QT interval and ST segment elevation by amplifying the region of the CACNA1C DNA or RNA encoding amino acid 39 of the CACNA1C polypeptide and sequencing the amplified DNA or RNA wherein substitution of nucleic acid encoding valine at position 39 is indicative of shorter than normal QT interval and ST segment elevation.

Polymorphisms can lead to subclinical forms of shorter than normal QT interval and ST segment elevation, which may manifest only after exposure to certain drugs or environmental factors. As such, the identification of a polymorphism allows practitioners to counsel patients to avoid these drugs or environmental factors.

Also provided is an isolated nucleic acid coding for a mutant CACNB2b polypeptide which causes shorter than normal QT interval and ST segment elevation. In one embodiment, the nucleic acid encodes a mutant CACNB2b polypeptide containing a substitution of leucine for serine at position 481. In one embodiment, the DNA coding for a mutant CACNB2b polypeptide contains a substitution of either C for T at nucleotide position 1442 of the wild-type CACNB2b gene. A vector containing such isolated nucleic acid is also provided. A cell transformed or transfected with such isolated nucleic acid is also provided. Also provided is a nucleic acid probe which will hybridize to said isolated nucleic acid. Also provided is an isolated mutant CACNB2b polypeptide containing a substitution of leucine for serine at position 481.

Also provided is an isolated nucleic acid coding for a mutant CACNA1C polypeptide which causes shorter than normal QT interval and ST segment elevation. In one embodiment, the nucleic acid encodes a mutant CACNA1C polypeptide containing a substitution of arginine for glycine at position 490. In one embodiment, the DNA coding for a mutant CACNA1C polypeptide contains a substitution of A for G at nucleotide position 1468 in exon 10 of the wild-type CACNA1C gene. A vector containing such isolated nucleic acid is also provided. A cell transformed or transfected with such isolated nucleic acid is also provided. Also provided is a nucleic acid probe which will hybridize to said isolated nucleic acid. Also provided is an isolated mutant CACNA1C polypeptide containing a substitution of arginine for glycine at position 490.

Also provided is an isolated nucleic acid coding for a mutant CACNA1C polypeptide which causes shorter than normal QT interval and ST segment elevation. In one embodiment, the nucleic acid encodes a mutant CACNA1C polypeptide containing a substitution of valine for alanine at position 39. In one embodiment, the DNA coding for a mutant CACNA1C polypeptide contains a substitution of C for T at nucleotide position 116 in exon 2 of the wild-type CACNA1C gene. A vector containing such isolated nucleic acid is also provided. A cell transformed or transfected with such isolated nucleic acid is also provided. Also provided is a nucleic acid probe which will hybridize to said isolated nucleic acid. Also provided is an isolated mutant CACNA1C polypeptide containing a substitution of valine for alanine at position 490.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

It is known that there are numerous splice variants of the $\alpha_1$ and $\beta_{2b}$ subunits of the L-type calcium channel polypeptides with channel activity. See, e.g., Foell et al., *Physiol Genomics*, 2004; 17:183-200; Splawski et al., *Cell*. 2004; 119:19-31. As used herein, functional CACNA1C polypeptide splice variants exhibit L-type calcium channel activity. Likewise, as used herein, functional CACNB2b polypeptide splice variants exhibit L-type calcium channel activity. To "exhibit L-type calcium channel activity" is to have a similar level of functional activity as the wild type polypeptides, with the exception that, in the case of the mutants described herein, there is manifest a shorter than normal QT interval and ST segment elevation. Accordingly, reference to "wild type CACNA1C", "wild type CACNB2b", "mutant CACNA1C" or "mutant CACNB2b" herein is meant to include functional splice variants of the same. Thus, in one embodiment, functional mutant CACNA1C polypeptide splice variants according to the present invention include a polypeptide fragment, AAAGLVPEHIP (SEQ. ID. NO. 3), which contains the substitution of valine for alanine as compared to the wild-type sequence. It should be understood that in SEQ. ID. NO. 1, which corresponds to the wild type CACNA1C polypeptide, the substitution is at position 39, but that in functional splice variants, the position may shift as long as the polypeptide exhibits L-type calcium channel activity as described herein. In another embodiment, functional mutant CACNA1C polypeptide splice variants according to the present invention include a polypeptide fragment, EGENCRARLAH (SEQ. ID. NO. 4), which contains the substitution of arginine for glycine as compared to the wild-type sequence. It should be understood that in SEQ. ID. NO. 1, the substitution is at position 490, but that in functional splice variants, the position may shift as long as the polypeptide exhibits L-type calcium channel activity as described herein. In another embodiment, functional mutant CACNB2b polypeptide splice variants according to the present invention include a polypeptide fragment, HRSSSLAPHHN (SEQ. ID. NO. 5), which contains the substitution of leucine for serine as compared to the wild-type sequence. It should be understood that in SEQ. ID. NO. 2, which corresponds to the wild type CACNB2b polypeptide, the substitution is at position 481, but that in functional splice variants, the position may shift as long as the polypeptide exhibits L-type calcium channel activity as described herein.

"Isolated", as used herein, means that the original material to which it refers was removed from the environment where it may have originally been found. "Isolated" material also includes material which may have originally been found in a native environment but was synthesized outside that native environment by artificial means. Such "isolated" materials may be combined with other materials. Thus, for example, an "isolated" nucleic acid is still considered to be "isolated" even if it is found in a self-replicating cell that is the progeny of a parent cell that was transformed or transfected with nucleic acid that was not native to that parent cell.

In determining existence of shorter than normal QT interval and ST segment elevation syndrome, probands with Brugada syndrome were screened for ion channel gene mutations using direct sequencing. Site-directed mutagenesis was performed and CHO-K1 cells were co-transfected with cDNAs encoding WT or mutant CACNB2b ($Ca_v\beta_{2b}$), CACNA2D1 ($Ca_v\alpha_2\delta_1$) and CACNA1C tagged with enhanced yellow fluorescent protein ($Ca_v1.2$). Whole-cell patch clamp studies were performed after 48-72 hours.

Certain individuals displaying ST segment elevation and QTc intervals ≦360 ms had mutations in genes encoding the cardiac L-type calcium channel. QTc ranged from 330 to 370 ms among probands and clinically affected family members. Rate adaptation of QT interval was reduced. Quinidine normalized the QT interval and prevented stimulation-induced ventricular tachycardia. Genetic and heterologous expression studies revealed loss of function missense mutations in CACNA1C (A39V and G490R) and CACNB2 (S481L) encoding the $\alpha_1$ and $\beta_{2b}$ subunits of the L-type calcium channel. Confocal microscopy revealed a defect in trafficking of A39V $Ca_v1.2$ channels but normal trafficking of channels containing G490R $Ca_v1.2$ or S481L $Ca_v\beta_{2b}$ subunits. This is the first report of loss of function mutations in genes encoding the cardiac L-type calcium channel to be associated with a familial sudden cardiac death syndrome in which a Brugada syndrome phenotype is combined with shorter than normal QT intervals.

Accordingly, a method of screening compounds for use in treating cardiac ion channel abnormalities resulting from the mutations described herein is provided. In one aspect, patients who have been diagnosed with one or more of the mutations described herein are dosed with a pharmaceutically acceptable compound which an investigator suspects may have an effect on the ion channel, an electrocardiogram is taken, and the effect of the QT interval and ST segment, if any, is ascertained. A therapeutic effect is considered one which modifies an abnormal interval to a more normal interval.

In another aspect, a cell based assay is provided. Cells containing nucleic acid encoding mutant CACNA1C and/or CACNB2 polypeptide as described herein are contacted with a test compound and the effect on ion channel currents is ascertained. Suitable cells include, e.g., human embryonic kidney cells (HEK) and cardiac cell lines such as HL-1, described in U.S. Pat. No. 6,316,207, incorporated herein by reference. Other modalities include transfected oocytes or transgenic animals. A test compound is added to the cells in culture or administered to a transgenic animal containing mutant CACNA1C and/or CACNB2 and the effect on the current of the ion channel is compared to the current of a cell or animal containing the wild-type CACNA1C and/or CACNB2. Drug candidates which alter the current to a more normal level are useful for treating or preventing shorter than normal QT interval and ST segment elevation syndrome.

According to the diagnostic and prognostic methods of the present invention, alteration of the wild-type CACNA1C and/or CACNB2 genes and/or polypeptides are detected. Useful diagnostic techniques include, but are not limited to fluorescent in situ hybridization (FISH), direct nucleic acid sequencing, PFGE analysis, Southern blot analysis, single stranded conformation analysis (SSCA), RNase protection assay, allele-specific oligonucleotide (ASO), dot blot analysis, hybridization using nucleic acid modified with gold nanoparticles and PCR-SSCP. Also useful is the recently developed technique of DNA microarray technology. Implementation of these techniques is considered to be routine for those skilled in the art.

The presence of sudden cardiac death or susceptibility thereto may be ascertained by testing any tissue of a human subject or non-human subject for mutations of the CACNA1C and/or CACNB2 genes or polypeptides as described herein. For example, a person who has inherited a germline CACNA1C and/or CACNB2 mutation as described herein would be prone to have shorter than normal QT interval and ST segment elevation syndrome, to develop arrhythmias, syncope or suffer from sudden cardiac death depending on the particular mutation. This can be determined by testing DNA from any tissue of the subject's body. Most simply, blood can be drawn and DNA extracted from the cells of the blood. In addition, prenatal diagnosis can be accomplished by testing fetal cells, placental cells or amniotic cells for mutations of the CACNA1C and/or CACNB2 genes. Alteration of a wild-type CACNA1C and/or CACNB2 gene, whether, for example, by point mutation or deletion, can be detected by any of the means discussed herein.

Those skilled in the art are familiar with numerous methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., Proc. Natl. Acad. Sci. USA 86:2766-2770 (1989)). This method does not detect all sequence changes, especially if the DNA fragment size is greater than 200 bp, but can be optimized to detect most DNA sequence variation. The reduced detection sensitivity may be a disadvantage, but the increased throughput possible with SSCP can make it an attractive, viable alternative to direct sequencing for mutation detection. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., Am. J. Hum. Genet. 49:699-706 (1991)), heteroduplex analysis (HA) (White et al., Genomics 12:301-306 (1992)) and chemical mismatch cleavage (CMC) (Grompe et al., Proc. Natl. Acad. Sci. USA 86:5855-5892 (1989)). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., Science 277:1078-1081 (1997)).

Detection of point mutations described herein may be accomplished by molecular cloning of the CACNA1C and/or CACNB2 genes and sequencing the genes using techniques well known in the art. Also, the gene or portions of the gene may be amplified, e.g., by PCR or other amplification technique, and the amplified gene or amplified portions of the gene may be sequenced.

Well known methods for indirect, test for confirming the presence of a susceptibility mutant include: 1) single stranded conformation analysis (SSCP) (Orita M, et al. (1989) Proc. Natl. Acad. Sci. USA 86:2766-2770); 2) denaturing gradient gel electrophoresis (DGGE) (Wartell R M, et al. (1990) Nucl. Acids Res. 18:2699-2705; Sheffield V C, et al. (1989) Proc. Natl. Acad. Sci. USA 86:232-236); 3) RNase protection assays (Finkelstein J, et al. (1990) Genomics 7:167-172; Kinszler K W, et al. (1991) Science 251:1366-1370); 4) allele-specific oligonucleotides (ASOs) (Conner B J, et al. (1983) Proc. Natl. Acad. Sci. USA 80:278-282); 5) the use of proteins which recognize nucleotide mismatches, such as the *E. coli* mutS protein (Modrich P (1991) Ann. Rev. Genet. 25:229-253); and 6) allele-specific PCR (Ruano G and Kidd K K (1989) Nucl. Acids Res. 17:8392). For allele-specific PCR, primers are used which hybridize at their 3' ends to particular CACNA1C and/or CACNB2 gene mutations. If the particular mutation is not present, an amplification product is not observed. Amplification Refractory Mutation System (ARMS) can also be used. In addition, restriction fragment length polymorphism (RFLP) probes for the genes or surrounding marker genes can be used to score alteration of a mutant or an insertion in a polymorphic fragment. Such a method is useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences. Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. The method involves the use of a labeled riboprobe which is complementary to the respective human wild-type CACNA1C and/or CACNB2 gene coding sequences. The riboprobe and either mRNA or DNA isolated from the subject are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton R G, et al. (1988) Proc. Natl. Acad. Sci. USA 85:4397-4401; Shenk T E, et al. (1975) Proc. Natl. Acad. Sci. USA 72:989-993; Novack D F, et al. (1986) Proc. Natl. Acad. Sci. USA 83:586-590. Alternatively, mismatches can be detected by shifts in the electrophoretic mobility of mismatched duplexes relative to matched duplexes. See, e.g., Cariello N F (1988) Am. J. Human Genetics 42:726-734). With either riboprobes or DNA probes, the cellular mRNA or DNA which might contain a mutation can be amplified using PCR before hybridization. Changes in DNA of the CACNA1C and/or CACNB2 genes can also be detected using Southern hybridization.

DNA sequences of the CACNA1C and/or CACNB2 genes which have been amplified by use of PCR may also be screened using mutant-specific probes. These probes are nucleic acid oligomers, each of which contains a region of the gene sequence harboring any of the mutations described herein. For example, one oligomer may be about 30 nucleotides in length, corresponding to a portion of the gene sequence. By use of a battery of such probes, PCR amplification products can be screened to identify the presence of a previously identified mutation in the gene. Hybridization of probes with amplified CACNA1C and/or CACNB2 sequences can be performed, for example, on a nylon filter. Hybridization to a particular probe under high stringency hybridization conditions indicates the presence of the same mutation in the tissue as in the allele-specific probe. High stringency hybridization conditions may be defined as those conditions which allow an 8 basepair stretch of a first nucleic acid (a probe) to bind to a 100% perfectly complementary 8 basepair stretch of nucleic acid while simultaneously preventing binding of said first nucleic acid to a nucleic acid which is not 100% complementary, i.e., binding will not occur if there is a mismatch.

Thus, in one embodiment, the above-identified DNA sequences may be detected by DNA hybridization probe technology. In one example, which is not exclusive, the sample suspected of containing the genetic marker is spotted directly on a series of membranes and each membrane is hybridized with a different labeled oligonucleotide probe that is specific for the particular sequence variation. One procedure for spotting the sample on a membrane is described by Kafotos et al., Nucleic Acids Research, 7:1541-1552 (1979).

Briefly, the DNA sample affixed to the membrane may be pretreated with a prehybridization solution containing sodium dodecyl sulfate, Ficoll, serum albumin and various salts prior to the probe being added. Then, a labeled oligonucleotide probe that is specific to each sequence to be detected is added to a hybridization solution similar to the prehybridization solution. The hybridization solution is applied to the membrane and the membrane is subjected to hybridization conditions that will depend on the probe type and length, type and concentration of ingredients, etc. Generally, hybridization may be carried out at about 25-75° C., preferably 35 to 65° C., for 0.25-50 hours, preferably less than three hours. The greater the stringency of conditions, the greater the required complementarity for hybridization between the probe and sample. If the background level is high, stringency may be increased accordingly. The stringency can also be incorporated in the wash.

After the hybridization the sample is washed of unhybridized probe using any suitable means such as by washing one or more times with varying concentrations of standard saline phosphate EDTA (SSPE) (180 nM NaCl, 10 mM $Na_2 HPO_4$ and 1 M EDTA, pH 7.4) solutions at 25-75° C. for about 10 minutes to one hour, depending on the temperature. The label is then detected by using any appropriate detection techniques known to those skilled in the art.

The sequence-specific oligonucleotide that may be employed herein is an oligonucleotide that may be prepared using any suitable method, such as, for example, the organic synthesis of a nucleic acid from nucleoside derivatives. This synthesis may be performed in solution or on a solid support. One type of organic synthesis is the phosphotriester method, which has been utilized to prepare gene fragments or short genes. In the phosphotriester method, oligonucleotides are prepared that can then be joined together to form longer nucleic acids. For a description of this method, see, e.g., Narang, S. A., et al., Meth. Enzymol., 68, 90 (1979) and U.S. Pat. No. 4,356,270.

A second type of organic synthesis is the phosphodiester method, which has been utilized to prepare tRNA genes. See Brown, E. L., et al., Meth. Enzymol., 68, 109 (1979) for a description of this method. As in the phosphotriester method, the phosphodiester method involves synthesis of oligonucleotides that are subsequently joined together to form the desired nucleic acid.

Automated embodiments of these methods may also be employed. In one such automated embodiment diethylphosphoramidites are used as starting materials and may be synthesized as described by Beaucage et al., Tetrahedron Letters, 22:1859-1862 (1981). One method for synthesizing oligonucleotides on a modified solid support is described, e.g., in U.S. Pat. No. 4,458,066. It is also possible to use a primer which has been isolated from a biological source (such as a restriction endonuclease digest).

The sequence-specific oligonucleotide must encompass the region of the sequence which spans the nucleotide variation being detected and must be specific for the nucleotide variation being detected. For example, oligonucleotides may be prepared, each of which contains the nucleotide sequence site characteristic of each of the mutated DNA sequences herein. Each oligonucleotide would be hybridized to duplicates of the same sample to determine whether the sample contains one or more of the regions of the locus where the mutations described herein may occur which are characteristic of shorter than normal QT interval and ST segment elevation syndrome.

The length of the sequence-specific oligonucleotide will depend on many factors, including the source of oligonucleotide and the nucleotide composition. For purposes herein, the oligonucleotide typically contains 15-30 nucleotides, although it may contain more or fewer nucleotides. While oligonucleotides which are at least 19-mers in length may enhance specificity and/or sensitivity, probes which are less than 19-mers, e.g., 16-mers, show more sequence-specific discrimination, presumably because a single mismatch is more destabilizing. If amplification of the sample is carried out as described below prior to detection with the probe, amplification increases specificity so that a longer probe length is less critical, and hybridization and washing temperatures can be lowered for the same salt concentration. Therefore, in such a case it may be preferred to use probes which are less than 19-mers.

Where the sample is first placed on the membrane and then detected with the oligonucleotide, the oligonucleotide should be labeled with a suitable label moiety, which may be detected by spectroscopic, photochemical, biochemical, immunochemical or chemical means. Immunochemical means include antibodies which are capable of forming a complex with the oligonucleotide under suitable conditions, and biochemical means include polypeptides or lectins capable of forming a complex with the oligonucleotide under the appropriate conditions. Examples include fluorescent dyes, electron-dense reagents, enzymes capable of depositing insoluble reaction products or being detected chronogenically, such as alkaline phosphatase, a radioactive label such as $^{32}$P, or biotin. If biotin is employed, a spacer arm may be utilized to attach it to the oligonucleotide.

In a "reverse" dot blot format, a labeled sequence-specific oligonucleotide probe capable of hybridizing with one of the DNA sequences is spotted on (affixed to) the membrane under prehybridization conditions as described above. The sample is then added to the pretreated membrane under hybridization conditions as described above. Then the labeled oligonucleotide or a fragment thereof is released from the membrane in such a way that a detection means can be used to determine if a sequence in the sample hybridized to the labeled oligonucleotide. The release may take place, for example, by adding a restriction enzyme to the membrane which recognizes a restriction site in the probe. This procedure, known as oligomer restriction, is described more fully in EP Patent Publication 164,054 published Dec. 11, 1985, the disclosure of which is incorporated herein by reference.

Alternatively, a sequence specific oligonucleotide immobilized to the membrane could bind or "capture" a target DNA strand (PCR-amplified). This "captured" strand could be detected by a second labeled probe. The second oligonucleotide probe could be either locus-specific or allele-specific.

In an alternative method for detecting the DNA sequences herein, the sample to be analyzed is first amplified using DNA polymerase, nucleotide triphosphates and primers. Briefly, this amplification process involves the steps of: (a) treating a DNA sample suspected of containing one or more of the mutations described above, together or sequentially, with different nucleotide triphosphates, an agent for polymerization of the nucleotide triphosphates, and one deoxyribonucleotide primer for each strand of each DNA suspected of containing the abode described mutations under hybridizing conditions, such that for each DNA strand containing each different genetic marker to be detected, an extension product of each primer is synthesized which is complementary to each DNA strand, wherein said primer(s) are selected so as to be substantially complementary to each DNA strand containing each different genetic marker, such that the extension product synthesized from one primer, when it is separated from its complement, can serve as a template for synthesis of the extension product of the other primer; (b) treating the sample under denaturing conditions to separate the primer extension products from their templates if the sequence(s) to be detected are present; and (c) treating the sample, together or sequentially, with the nucleotide triphosphates, an agent for polymerization of the nucleotide triphosphates, and oligonucleotide primers such that a primer extension product is synthesized using each of the single strands produced in step (b) as a template, wherein steps (b) and (c) are repeated a sufficient number of times to result in detectable amplification of the nucleic acid containing the sequence(s) if present.

The sample is then affixed to a membrane and detected with a sequence-specific probe as described above. Preferably, steps (b) and (c) are repeated at least five times, and more preferably 15-30 times if the sample contains human genomic DNA. If the sample comprises cells, preferably they are heated before step (a) to expose the DNA therein to the reagents. This step avoids extraction of the DNA prior to reagent addition.

In a "reverse" dot blot format, at least one of the primers and/or at least one of the nucleotide triphosphates used in the amplification chain reaction is labeled with a detectable label, so that the resulting amplified sequence is labeled. These labeled moieties may be present initially in the reaction mixture or added during a later cycle. Then an unlabeled sequence-specific oligonucleotide capable of hybridizing with the amplified sequence(s), if the sequence(s) is/are present, is spotted on (affixed to) the membrane under prehybridization conditions as described above. The amplified sample is then added to the pretreated membrane under hybridization conditions as described above. Finally, detection means are used to determine if an amplified sequence in the DNA sample has hybridized to the oligonucleotide affixed to the membrane. Hybridization will occur only if the membrane-bound sequence containing the variation is present in the amplification product.

Variations of this method include use of an unlabeled PCR target, an unlabeled immobilized allele-specific probe and a labeled oligonucleotide probe in a sandwich assay.

The amplification method provides for improved specificity and sensitivity of the probe; an interpretable signal can be obtained with a 0.04 µg sample in six hours. Also, if the amount of sample spotted on a membrane is increased to 0.1-0.5 µg, non-isotopically labeled oligonucleotides may be utilized in the amplification process rather than the radioactive probes used in previous methods. Finally, as mentioned above, the amplification process may be applicable to use of sequence-specific oligonucleotides less than 19-mers in size, thus allowing use of more discriminatory sequence-specific oligonucleotides.

In a variation of the amplification procedure, a thermostable enzyme, such as one purified from *Thermus aquaticus*, may be utilized as the DNA polymerase in a temperature-cycled chain reaction. The thermostable enzyme refers to an enzyme which is stable to heat and is heat resistant and catalyzes (facilitates) combination of the nucleotides in the proper manner to form the primer extension products that are complementary to each DNA strand.

In this latter variation of the technique, the primers and nucleotide triphosphates are added to the sample, the mixture is heated and then cooled, and then the enzyme is added, the mixture is then heated to about 90-100° C. to denature the DNA and then cooled to about 35-40° C., and the cycles are repeated until the desired amount of amplification takes place. This process may also be automated. The amplification process using the thermostable enzyme is described more fully in U.S. Pat. No. 4,965,188, which is incorporated herein by reference.

The invention herein also contemplates a kit format which includes a packaged multicontainer unit having containers for each labeled sequence-specific DNA probe. The kit may optionally contain a means to detect the label (such as an avidin-enzyme conjugate and enzyme substrate and chromogen if the label is biotin). In addition, the kit may include a container that has a positive control for the probe containing one or more DNA strands with the sequence to be detected and a negative control for the probe that does not contain the DNA strands having any of the sequences to be detected.

Nucleic acid analysis via microarray technology is also applicable to the present invention. In this technique, literally thousands of distinct oligonucleotide probes are built up in an array on a silicon chip. Nucleic acid to be analyzed labeled, e.g., fluorescently, and hybridized to the probes on the chip. It is also possible to study nucleic acid-protein interactions using these nucleic acid microarrays. Using this technique one can determine the presence of mutations or even sequence the nucleic acid being analyzed or one can measure expression levels of a gene of interest. The method is one of parallel processing of many, even thousands, of probes at once and can tremendously increase the rate of analysis.

One method for detecting the amino acid sequences in a protein sample that are associated with shorter than normal QT interval and ST segment elevation syndrome as described herein involves the use of an immunoassay employing one or more antibodies that bind to one or more of the mutated amino acid sequences. While the antibodies may be polyclonal or monoclonal, monoclonal antibodies are preferred in view of their specificity and affinity for the antigen.

Polyclonal antibodies may be prepared by well-known methods which involve synthesizing a peptide containing one or more of the amino acid sequences described herein as associated with shorter than normal QT interval and ST segment elevation syndrome, purifying the peptide, attaching a carrier protein to the peptide by standard techniques, and injecting a host such as a rabbit, rat, goat, mouse, etc. with the peptide. The sera are extracted from the host by known methods and screened to obtain polyclonal antibodies which are specific to the peptide immunogen. The peptide may be synthesized by the solid phase synthesis method described by Merrifield, R. B., Adv. Enzymol. Relat. Areas Mol. Biol., 32:221-296 (1969) and in "The Chemistry of Polypeptides" (P. G. Katsoyannis, ed.), pp. 336-361, Plenum, New York (1973), the disclosures of which are incorporated herein by reference. The peptide is then purified and may be conjugated to keyhold limpet hemocyanin (KLH) or bovine serum albumin (BSA). This may be accomplished via a sulfhydryl group, if the peptide contains a cysteine residue, using a heterobifunctional crosslinking reagent such as N-maleimido-6-amino caproyl ester of 1-hydroxy-2-nitrobenzene-4-sulfonic acid sodium salt.

The monoclonal antibody will normally be of rodent or human origin because of the availability of murine, rat, and human tumor cell lines that may be used to produce immortal hybrid cell lines that secrete monoclonal antibody. The antibody may be of any isotype, but is preferably an IgG, IgM or IgA, most preferably an IgG2a.

The murine monoclonal antibodies may be produced by immunizing the host with the peptide mentioned above. The host may be inoculated intraperitoneally with an immunogenic amount of the peptide and then boosted with similar amounts of the immunogenic peptide. Spleens or lymphoid tissue is collected from the immunized mice a few days after the final boost and a cell suspension is prepared therefrom for use in the fusion.

Hybridomas may be prepared from the splenocytes or lymphoid tissue and a tumor (myeloma) partner using the general somatic cell hybridization technique of Koehler, B. and Milstein, C., Nature, 256:495-497 (1975) and of Koehler, B. et al., Eur. J. Immunol., 6:511-519 (1976). Suitable myeloma cells for this purpose are those which fuse efficiently, support stable, high-level expression of antibody by the selected antibody-producing cells, and are sensitive to a medium such as HAT medium. Among these, suitable myeloma cell lines are murine myeloma lines, such as those derived from MOPC-21 and MOPC-11 mouse tumors available from the Salk Institute, Cell Distribution Center, San Diego, Calif., USA, or P3×63-Ag8.653 (653) and Sp2/0-Ag14 (SP2/0) myeloma lines available from the American Type Culture Collection, Rockville, Md., USA, under ATCC CRL Nos. 1580 and 1581, respectively.

Basically, the technique may involve fusing the appropriate tumor cells and splenocytes or lymphoid tissue using a fusogen such as polyethylene glycol. After the fusion the cells are separated from the fusion medium and grown on a selective growth medium, such as HAT medium, to eliminate unhybridized parent cells and to select only those hybridomas that are resistant to the medium and immortal. The hybridomas may be expanded, if desired, and supernatants may be assayed by conventional immunoassay procedures (e.g., radioimmunoassay, enzyme immunoassay, or fluorescence immunoassay) using the immunizing agent as antigen. Positive clones may be characterized further to determine whether they meet the criteria of the antibodies of the invention. For example, the antigen-binding ability of the antibodies may be evaluated in vitro by immunoblots, ELISAs and antigen neutralizing tests.

An example of a suitable procedure for making a hybrid cell line that secretes human antibodies against the amino acid genetic markers is somatic cell hybridization using a mouse× human parent hybrid cell line and a human cell line producing sufficiently high levels of such antibodies. The human cell line may be obtained from volunteers immunized with the peptide(s) described above. The human cell line may be transformed with Epstein-Barr virus (EBV) as described, for example, by Foung, et al., J. Immunol. Methods, 70:83-90 (1984).

When EBV transformation is employed, the most successful approaches have been either to pre-select the population of B cells to be transformed or to post-select the antigen-specific transformed populations by panning or rosetting techniques, as described by Kozbar, et al., Scan. J. Immunol., 10:187-194 (1979) and Steinitz, et al., J. Clin. Lab. Immun., 2:1-7 (1979). EBV transformation has been combined with cell fusion to generate human monoclonal antibodies (see, e.g., Foung et al., J. Immun. Meth., 70:83-90 (1984)), due to instability of immunoglobulin secretion by hybridomas when compared to EBV lymphoblastoid cell lines, and higher frequencies of rescue of the antigen-specific populations. EBV most frequently infects and transforms IgM-bearing B cells, but B cells secreting other classes of Ig can also be made into long-term lines using the EBV fusion technique, as described by Brown and Miller, J. Immunol., 128:24-29 (1982).

The cell lines which produce the monoclonal antibodies may be grown in vitro in suitable culture medium such as Iscove's medium, Dulbecco's Modified Eagle's Medium, or RPMI-1640 medium from Gibco, Grand Island, N.Y., or in vivo in syngeneic or immunodeficient laboratory animals. If desired, the antibody may be separated from the culture medium or body fluid, as the case may be, by conventional techniques such as ammonium sulfate precipitation, hydroxyapatite chromatography, ion exchange chromatography, affinity chromatography, electrophoresis, microfiltration, and ultracentrifugation.

The antibodies herein may be used to detect the presence or absence of one or more of the amino acid mutations described herein as associated with shorter than normal QT interval and ST segment elevation syndrome. The cells may be incubated in the presence of the antibody, and the presence or absence and/or degree of reaction (antibody-peptide binding) can be determined by any of a variety of methods used to determine or quantitate antibody/antigen interactions (e.g., fluorescence, enzyme-linked immunoassay (ELISA), and cell killing using antibody and complement by standard methods). The antibody employed is preferably a monoclonal antibody.

For use in solid phase immunoassays, the antibodies employed in the present invention can be immobilized on any appropriate solid test support by any appropriate technique. The solid test support can be any suitable insoluble carrier material for the binding of antibodies in immunoassays. Many such materials are known in the art, including, but not limited to, nitrocellulose sheets or filters; agarose, resin, plastic (e.g., PVC or polystyrene) latex, or metal beads; plastic vessels; and the like. Many methods of immobilizing antibodies are also known in the art. See, e.g., Silman et al., Ann. Rev. Biochem., 35:873 (1966); Melrose, Rev. Pure & App. Chem., 21:83 (1971); Cuatrecafas, et al., Meth. Enzym., Vol. 22 (1971). Such methods include covalent coupling, direct adsorption, physical entrapment, and attachment to a protein-coated surface. In the latter method, the surface is first coated with a water-insoluble protein such as zein, collagen, fibrinogen, keratin, glutelin, etc. The antibody is attached by simply contacting the protein-coated surface with an aqueous solution of the antibody and allowing it to dry.

Any combination of support and binding technique which leaves the antibody immunoreactive, yet sufficiently immobilizes the antibody so that it can be retained with any bound antigen during a washing, can be employed in the present invention. A preferred solid test support is a plastic bead.

In the sandwich immunoassay, a labeled antibody is employed to measure the amount of antigen bound by the immobilized monoclonal antibody. The label can be any type that allows for the detection of the antibody when bound to a support. Generally, the label directly or indirectly results in a signal which is measurable and related to the amount of label present in the sample. For example, directly measurable labels can include radiolabels (e.g., $^{125}$I, $^{35}$S, $^{14}$C, etc.). A preferred directly measurable label is an enzyme, conjugated to the antibody, which produces a color reaction in the presence of the appropriate substrate (e.g., horseradish peroxidase/o-phenylenediamine). An example of an indirectly measurable label would be antibody that has been biotinylated. The presence of this label is measured by contacting it with a solution containing a labeled avidin complex, whereby the avidin becomes bound to the biotinylated antibody. The label associated with the avidin is then measured. A preferred example of an indirect label is the avidin/biotin system employing an enzyme conjugated to the avidin, the enzyme producing a color reaction as described above. It is to be understood, however, that the term "label" is used in its broadest sense and can include, for example, employing "labeled" antibodies where the label is a xenotypic or isotypic difference from the immobilized antibody, so that the presence of "labeled" antibodies is detectable by incubation with an anti-xenotypic or anti-isotypic antibody carrying a directly detectable label.

Whatever label is selected, it results in a signal which can be measured and is related to the amount of label in a sample. Common signals are radiation levels (when radioisotopes are used), optical density (e.g., when enzyme color reactions are used), and fluorescence (when fluorescent compounds are used). It is preferred to employ a nonradioactive signal, such as optical density (or color intensity) produced by an enzyme reaction. Numerous enzyme/substrate combinations are known in the immunoassay art which can produce a suitable signal. See, e.g., U.S. Pat. Nos. 4,323,647 and 4,190,496, the disclosures of which are incorporated herein.

For diagnostic use, the antibodies may typically be distributed in multicontainer kit form. These kits will typically contain the antibody(ies) in labeled or unlabeled form in suitable containers, any detectable ligand reactive with unlabeled antibody if it is used, reagents for the incubations and washings if necessary, reagents for detecting the label moiety to be detected, such as substrates or derivatizing agents depending on the nature of the label, product inserts and instructions, and a positive control associated with shorter than normal QT interval and ST segment elevation syndrome. The antibodies in the kit may be affinity purified if they are polyclonal.

The following examples are included for purposes of illustrating certain aspects of the invention. Accordingly, the examples should not be construed as limiting the subject matter of the present invention.

EXAMPLES

Patients were diagnosed with Brugada syndrome based on established criteria. See, Wilde et al., *Circulation*. 2002; 106: 2514-2519; Antzelevitch et. al., *Circulation*. 2005; 111:659-670. Eighty-two consecutive probands with a clinical diagnosis of Brugada syndrome enrolled in our registry were systematically screened for ion channel gene mutations. We define short QT as QTc intervals ≦360 ms for males and ≦370 ms for females, based on published reports. See, Rautaharju et al., Can J Cardiol. 1992; 8:690-695; Viskin et al., *Heart Rhythm*. 2004; 1:587-591. At a heart rate of 60 bpm, the predicted QT interval (QTp) is 410 msec and the lower limit of normal is defined as two standard deviations below QTp or 360. Clinical and genetic studies were performed in accordance with human subject guidelines after written informed consent according to protocols approved by the local Institutional Review Boards.

ECG Measurement

The ECG was digitally scanned, magnified 4 to 8 times, and measured using digital calipers. The end of the T wave was defined as the intersection of a tangent, drawn to the descending portion of the T-wave, with the isoelectric line. QT intervals were measured in lead II whenever possible.

Mutation Analysis

Genomic DNA was prepared from peripheral blood lymphocytes of patients 1, 2 and 3 and available family members. All known exons of known and candidate LQTS genes were amplified using intronic primers and sequenced in both directions to probe for mutations. The following genes were screened: SCN5A, SCN1B, SCN3B, KCNH2, KCNQ1, KCNJ2, KCNE1, KCNE2, KCNE3, KCND3 ($K_v4.3$), KCNIP2 (KCHiP2), KCNJ11, CACNA1C ($Ca_v1.2$), CACNB2b ($Ca_v\beta_{2b}$), and CACNA2D1 ($Ca_v\alpha_2\delta_1$). In addition, IRX5 was probed because of association of this transcriptional factor gene with Kv4 transient outward potassium channels. See, Costantini et al., *Cell*. 2005; 123:347-358.

All individuals studied in the control groups for the different mutations, matched by race and ethnic background, were healthy and had no family history of cardiac arrhythmias based on written clinical history. ECGs of control individuals were not available.

Mutagenesis and Transfection

Site-directed mutagenesis was performed using QuikChange (Stratagene, LaJolla, Calif.) on full-length human wild type (WT) CACNA1C cDNA cloned in pcDNA3 containing Exon 8 (accession number AJ224873), the CACNA1C clone (EYFP)$N\alpha_{1C.77}$, containing Exon 8A (accession number Z34815) and CACNB2b cloned in pcDNA3 (accession number AF285239) that were a kind gift from Dr. Nikolai Soldatov. CHO-K1 cells were grown in GIBCO F12 Nutrient Mixture in 35 mm culture dishes and placed in a 5% $CO_2$ incubator at 37° C. The cells were co-transfected with Lipofectamine or FuGene6 using a 1:1:1 molar ratio of WT or mutant human CACNA1C, CACNB2b and WT CACNA2D1. Splawski et al., *Cell*. 2004; 119:19-31. To assess the influence of WT on expression of the mutant channels, CHO-K1 cells were co-transfected with a combination of mutant and WT CACNA1C or mutant and WT CACNB2b using the same total molar ratio. Electrophysiological studies were performed after 48-72 hours of incubation. CACNA1C was transfected as either (EYFP)$N\alpha_{1C.77}$ or pcDNA3-CACNA1C. In the latter case, 0.86 μg of enhanced green fluorescent protein (EGFP) cDNA was added to the transfection mixture. The two approaches yielded similar electrophysiological results. It is noteworthy that previous studies have demonstrated that the fusion YFP ((EYFP)$N\alpha_{1C.77}$) did not influence $Ca_v1.2$ channel expression. Kobrinsky et al., *J Biol Chem*. 2005; 280:12474-12485.

Previous studies have shown that transmembrane segment 6 in domain I of $Ca_v1.2$ can be encoded by two mutually exclusive exons, 8 and 8A. Zuhlke et al., *FEBS Lett*. 1998; 427:220-224. Exon 8 is highly expressed in the heart and to a much lesser extent in other tissues. Splawski et al., *Proc Natl Acad Sci USA*. 2005; 102:8089-8096 ("Splawski I"). By comparison, exon 8A expression is less prominent in heart, but more impressive in organs with smooth muscle including the aorta, bladder, and uterus. Splawski et al., *Cell*. 2004; 119: 19-31 ("Splawski II"). Specific mutations in either splice variant cause a gain of function in $Ca_v1.2$ responsible for two forms of Timothy syndrome a multi-organ disease with severe QT prolongation, arrhythmia and sudden death. See, Splawski I and Splawski II.

Electrophysiology

Voltage clamp recordings from transfected CHO-K1 cells were made using patch pipettes, fabricated from 1.5 mm O.D. borosilicate glass capillaries, filled with a solution containing (mM/L): 120 $CsCl_2$, 2.0 $MgCl_2$, 10 HEPES, 5 $CaCl_2$, 2 MgATP and 10 EGTA, (pH 7.25 with CsOH) and had a resistance of 2-4 MΩ. Extracellular solution contained (mM/L): 130 NMDG, 5 KCl, 15 $CaCl_2$, 1 $MgCl_2$, 10 HEPES, pH 7.35 with HCl. Current signals were recorded using an Axopatch 200A or MultiClamp 700A amplifier (Axon Instruments Inc., Foster City, Calif.) and series resistance errors were reduced by 60-70% with electronic compensation. All recordings were made at room temperature.

Data Acquisition and Analysis

All signals were acquired at 20-50 kHz and analyzed with a PC running pCLAMP 9 software (Axon Instruments Inc., Foster City, Calif.). Results from pooled data are presented as Mean±S.E.M. and n represents the number of cells in each experiment. Statistical analysis was performed using ANOVA followed by a Student-Newman-Keuls test using SigmaStat software. A $p<0.05$ was considered statistically significant.

Localization of $Ca^{2+}$ Channels.

Confocal microscopy was used to assess trafficking of $Ca^{2+}$ channels tagged with enhanced yellow fluorescent protein (EYFP). Cells were grown on polylysine coated 35 mm glass culture dishes and studied 3 days post-transfection. Experiments were performed on an Olympus FluoView laser-scanning confocal microscope (Olympus America) and images were acquired with FluoView acquisition software. EYFP labelled cells were analyzed in the XYZ configuration. A region of interest (ROI) measurement confined to within 2 μm of the sarcolemma was made and the average pixel intensity within this ROI was defined as peripheral staining. The average pixel intensity for the remaining portion of the cell was also determined and defined as central staining. The ratio of peripheral:central fluorescence was calculated. Measurements were not normalized to cell area.

Rate-Dependence of the QT Interval

The rate-dependence of the QT Interval was evaluated during a standard exercise stress test with a bicycle ergometer or treadmill.

Results

Of the eighty-two consecutive probands with a clinical diagnosis of Brugada syndrome enrolled in our registry, 7 probands (8.5%) were found to have mutations in genes encoding the $\alpha_1$ and $\beta_{2b}$ subunits of the cardiac L-type calcium channel. In addition to ST segment elevation and a family history of sudden cardiac death, three of the 7 probands exhibited QTc intervals ≦360 msec. The present study is focused on delineation of the clinical characteristics and genetic basis for this distinct clinical entity.

The first proband (III-6), a 25 y/o Caucasian male, presented with aborted SCD. QTc was 330 ms and a coved-type ST segment elevation was observed in V1 and V2 following an ajmaline challenge (FIG. 1A). His 23 y/o brother (III-5) was also symptomatic with syncope since age 21. Programmed atrial stimulation induced atrial fibrillation in both individuals, and AV nodal reentrant tachycardia in the brother. The rest of the family was asymptomatic. The proband received an implantable cardioverter defibrillator (ICD) and over a 3 year follow-up period suffered only inappropriate shocks that ceased following a cavo-tricuspid isthmus ablation. A total of ten family members were evaluated clinically and genetically and 6 were characterized as phenotype-positive based on the presence of ST segment elevation ≧2 mm at baseline or following ajmaline and a QTc≦360 ms in males and ≦370 ms in females (FIG. 1B). III-3 showed a prominent r' in V2 at baseline and an ST segment elevation >2 mm in response to ajmaline that resulted in neither a coved or saddleback morphology; therefore the designation of +/−A. III-7, although genotype negative, showed a positive response to ajmaline; QTc was 414 ms. Tall peaked T waves were observed in some family members presenting with shorter than normal QT intervals. QT QT/heart rate slope was −0.639 ms/bpm for patient 1 (III-6) and −0.869 ms/bpm for the symptomatic brother of patient 3 (III-5).

Figure 3:
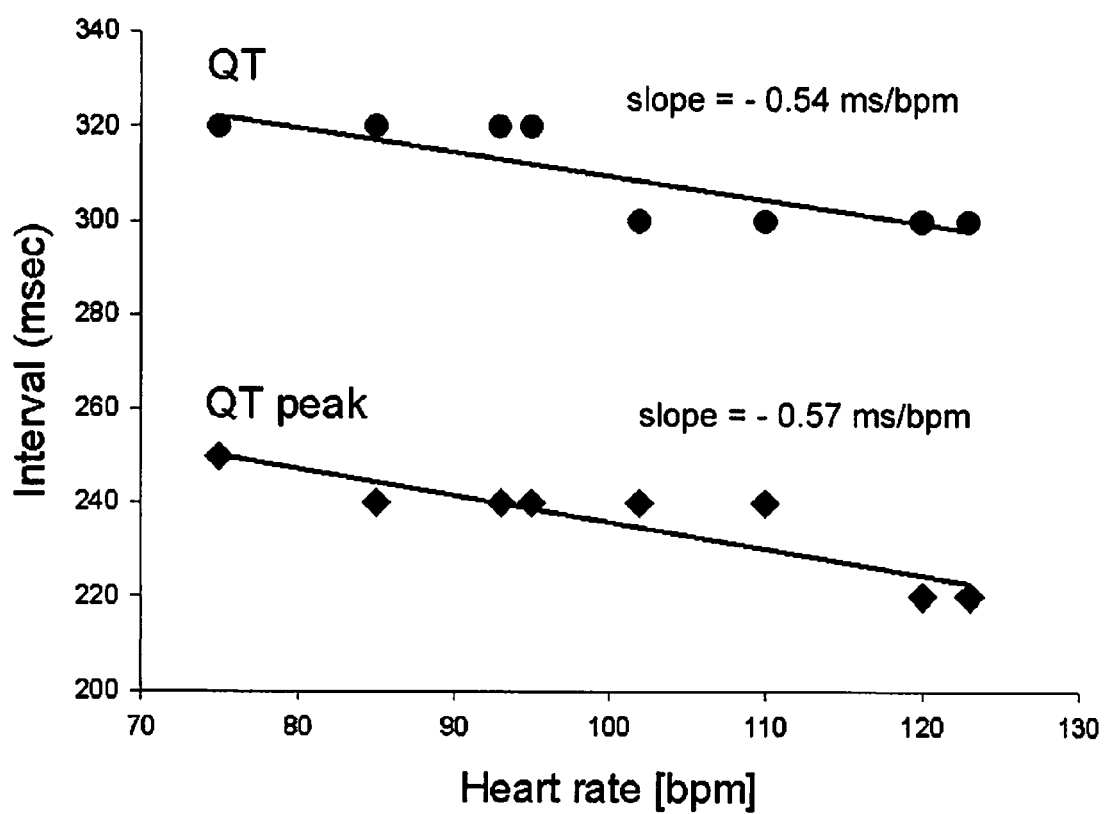
FIG. 3 is a graphical depiction of heart rate dependence of QT interval of patient 2. Plotted are the QTpeak and QTend (QT) intervals as a function of heart rate recorded during bicycle ergometry exercise test.

Patient 2, a 41 y/o Caucasian male of Turkish descent, presented with atrial fibrillation (AF) and an abbreviated QT interval of 300 ms (QTc=346 ms). His brother died from sudden cardiac arrest at age 45. Ajmaline administration (1 mg/kg) led to a further elevation of the ST segment in leads V1 to V2 (FIG. 1C). The QT interval showed little rate-dependence with a QT/heart rate slope of −0.54 ms/bpm (FIG. 3). Monomorphic VT was inducible with 2 extra-stimuli. Atrial and ventricular effective refractory period were 150 and 170 ms at 430 ms pacing cycle length. AH and HV-intervals and sinus node recovery time were within normal limits. Structural heart disease was ruled out by coronary angiography and right ventricular angiography. Quinidine (750 mg per day for 5 days), administered for control of AF, prolonged QTc to 390 ms. An implantable cardioverter defibrillator (ICD) was implanted for primary prevention. Programmed ventricular stimulation via the ICD lead was not able to induce ventricular tachycardia (VT) in the presence of quinidine. Patient 2 had several episodes of AF, but no ICD discharges during a one-year-follow-up.

Patient 3, a 44 y/o Caucasian male of European descent, presented with a prominent ST segment elevation in V1, a saddleback ST segment elevation in V2 and a prominent J wave in lead III (FIG. 1D). H is mother had 2 syncopal episodes at age 48 resulting in SCD. His father is 75 y/o with no known medical problems; brother (47 y/o), sister (44 y/o/) and three children (8, 10, 12 y/o) declined examination but reportedly do not exhibit the Brugada phenotype. Patient 3 was recently diagnosed with Facioscapulohumeral Muscular Dystrophy. His QTc was 360 ms and QT/heart rate slope was −0.991 ms/bpm.

In both patient 2 and 3, raising the position of the right precordial leads (V1-V3) two intercostal spaces unmasked or accentuated the Type I ST segment elevation in V1-V3 (FIGS. 1C and 1D).

All three probands displayed ejection fraction, sinus node recovery time and AV conduction values within normal limits.

Genetic analysis revealed no mutations in SCN5A, the gene traditionally associated with the Brugada syndrome (20% of cases), or KCNH2, KCNQ1 or KCNJ2, the genes previously linked to the short QT syndrome.

Figure 2:
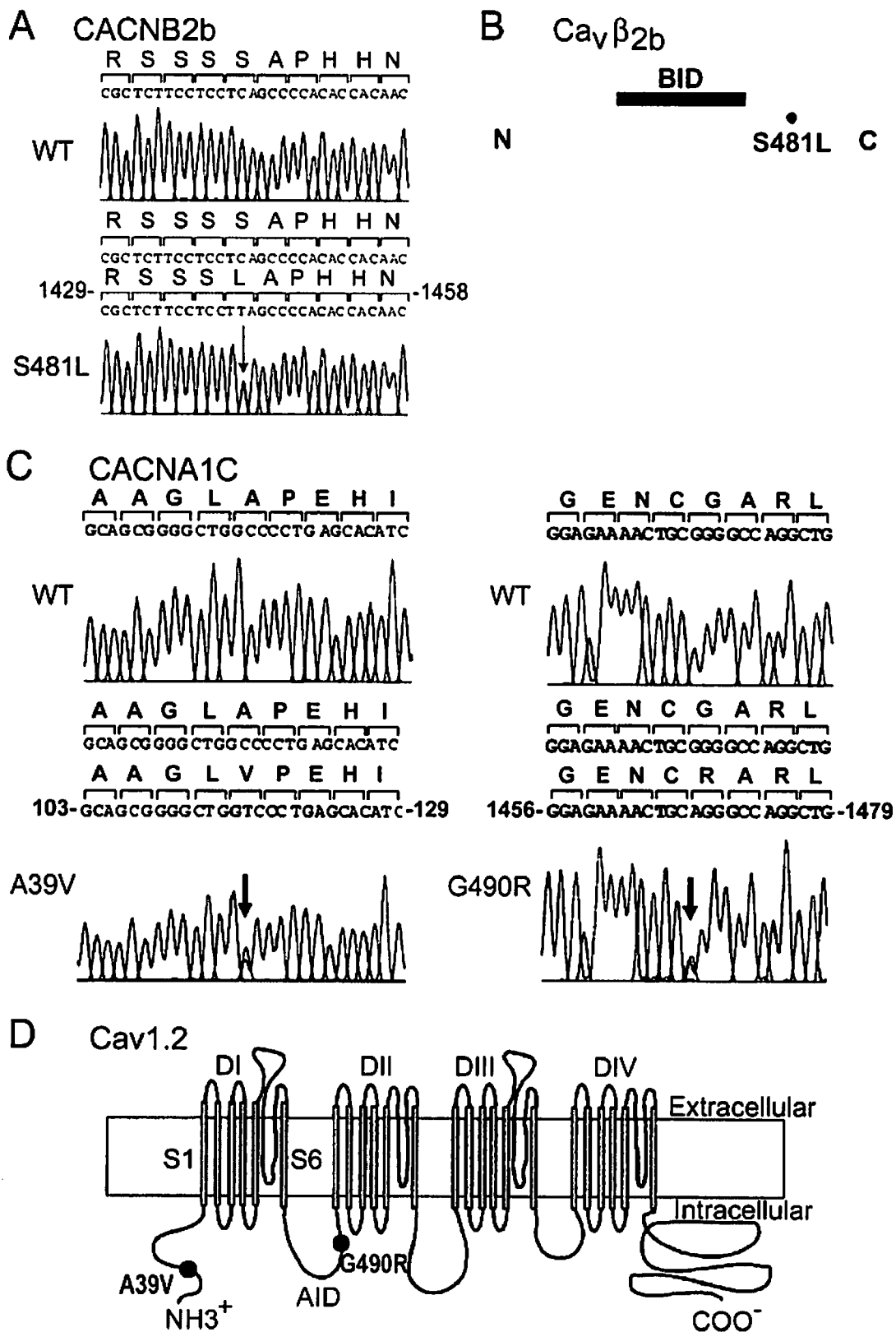
FIG. 2A depicts a DNA sequence analysis of heterozygous C1442T transition in exon 13 of CACNB2b evidencing replacement of serine by leucine at position 481.
FIG. 2B is a schematic depiction of $Ca_v\beta_{2b}$ (cytoplasmic) showing the location of the mutation and the position of the BID (beta subunit interaction domain) segment.
FIG. 2C depicts a DNA sequence analysis of heterozygous C to T transition (arrow) at position 116 in exon 2 of CACNA1C allele in Patient 2 evidencing a substitution of a valine for alanine at position 39 on the left, and heterozygous A to G transition (arrow) at position 1468 in exon 10 of CACNA1C allele in Patient 1 leads evidencing replacement of glycine by arginine at position 490 on the right.
FIG. 2D is a schematic depiction of the predicted topology of $Ca_v1.2$ showing the location of the mutations. The loop between domains I and II contains a conserved motif named "AID" (alpha subunit interaction domain) that binds to the beta subunit segment called "BID" (beta subunit interaction domain).

Patient 1 carried a heterozygous C1442T transition in exon 13 evidencing a substitution of leucine for serine at position 481 (S481L) of CACNB2b, which was not present in 400 ethnically matched control alleles (FIG. 2A). The mutation is located downstream of the β subunit interaction domain (BID) segment (FIG. 2B). The S48/L mutation was present in all 6 phenotype positive and absent in all 4 phenotype negative family members (FIG. 1B).

Patient 2 showed a heterozygous substitution of an adenine for a guanine at position 1468 in exon 10 of CACNA1C, evidencing substitution of an arginine for a glycine at position 490 (G490R) (FIG. 2C), which was not present in 640 ethnically-matched control alleles. Patient 2 also had two polymorphisms in CACNA1C, P1820L and V1821M, which were found in 31 and 27 of 114 healthy controls. The G490R mutation was also found in his two daughters (QTc=360 and 373). The daughter with the longer QTc interval (373 msec) also displayed a known polymorphism in KCNH2 (K897T).

Patient 3 showed a heterozygous C116T transition in exon 2 of CACNA1C, evidencing a substitution of a valine for an alanine at position 39, A39V (FIG. 2C), which was not present in 404 ethnically matched control alleles. In the proposed topology of the $Ca_v1.2$ channel subunit, the G490 is located in the cytoplasmic linker between domains I and II. A39 is located near the N-terminus of the protein (FIG. 2D). Both mutations are located within a highly conserved region of the $Ca_v1.2$ protein.

Figure 4:
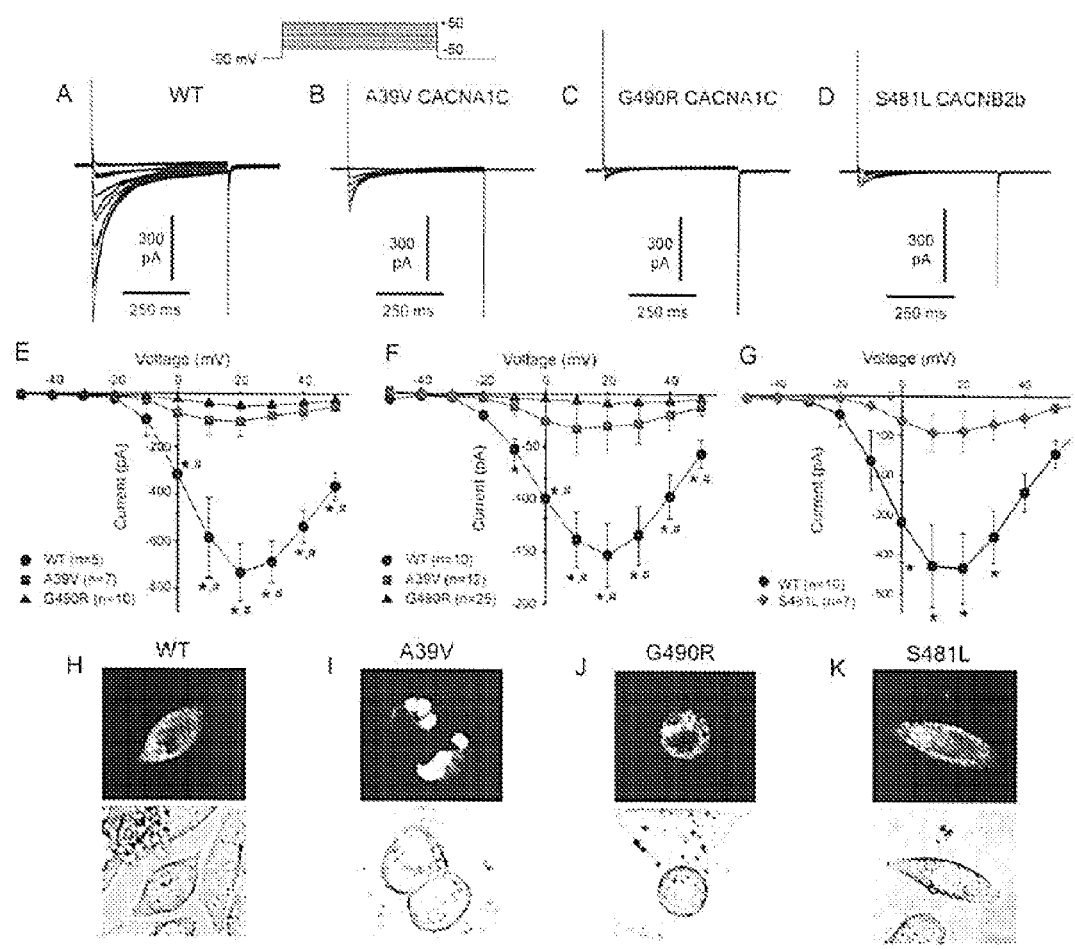
FIG. 4A is a graphical depiction of representative whole cell $Ca^{2+}$ currents recorded from CHO cells transfected with WT CACNA1C. Currents were elicited using the pulse protocol illustrated in the inset above FIG. 2B.
FIG. 4B is a graphical depiction of representative whole cell $Ca^{2+}$ currents recorded from CHO cells transfected with A39V mutant CACNA1C. Currents were elicited using the pulse protocol illustrated in the inset above FIG. 2B.
FIG. 4C is a graphical depiction of representative whole cell $Ca^{2+}$ currents recorded from CHO cells transfected with G490R mutant CACNA1C. Currents were elicited using the pulse protocol illustrated in the inset above FIG. 2B.
FIG. 4D is a graphical depiction of representative whole cell $Ca^{2+}$ currents recorded from CHO cells transfected with mutant CACNA1C and S481L mutant CACNB2b. Currents were elicited using the pulse protocol illustrated in the inset above FIG. 2B.
FIG. 4E is a graphical depiction of current-voltage (I-V) relationship for WT (n=5), A39V (n=7) and G490R (n=10) $Ca_v1.2$ channels (exon 8A variant).
FIG. 4F is a graphical depiction of current-voltage (I-V) relationship for WT (n=10), A39V (n=12) and G490R (n=25) $Ca_v1.2$ channels (exon 8 variant). *$p<0.05$ compared to G490R. # $p<0.05$ compared to A39V.
FIG. 4G is a graphical depiction of current-voltage (I-V) relationship for WT (n=10), S481L (n=7) $Ca_v\beta_{2b}$ channels. *$p<0.05$ compared to S481L.
FIG. 4H is a depiction of a representative confocal XYZ scan showing localization of EYFP-tagged $Ca_v1.2$ channels in a CHO cell expressing WT. $Ca_v1.2$ channels show marked peripheral and cytoplasmic fluorescence.
FIG. 4I is a depiction of a representative confocal XYZ scan showing localization of EYFP-tagged $Ca_v1.2$ channels in a CHO cell expressing A39V. $Ca_v1.2$ channels show fluorescence localized in the perinuclear region of the cell.
FIG. 4J is a depiction of a representative confocal XYZ scan showing localization of EYFP-tagged $Ca_v1.2$ channels in a CHO cell expressing G490R. $Ca_v1.2$ channels exhibit a fluorescence pattern similar to WT indicating that trafficking is not impaired.
FIG. 4K is a depiction of a representative confocal XYZ scan showing localization of EYFP-tagged $Ca_v1.2$ channels in a CHO cell expressing S481L. $Ca_v\beta_{2b}$ channels exhibit a fluorescence pattern similar to WT suggesting that trafficking is not impaired.

To determine the contribution of each mutation to the clinical phenotype, we expressed each of the WT and mutated CACNA1C and CACNB2b constructs in CHO cells and performed patch clamp experiments. We first compared the current-voltage (I-V) relationship between WT, A39V and 6490R channels in the EYFP-tagged, exon 8A variant of $Ca_v1.2$. A set of depolarizing pulses applied in 10 mV increments from a holding potential of −90 mV elicited robust WT currents. In contrast, the amplitudes of A39V and G490R currents were drastically reduced, although the voltage at peak current remained unchanged (FIG. 4E). Similar results were obtained when the exon 8 variant of $Ca_v1.2$ was used (FIG. 4F). CACNB2b WT and the S481L mutant were studied only with the EYFP-tagged, exon 8A variant of $Ca_v1.2$ (FIG. 4G). The results indicate that the two mutations in CACNA1C and the mutation in CACNB2b all cause a major loss of function in calcium channel activity.

To determine whether the mutation-induced loss of function was related to a trafficking defect, we used confocal microscopy to determine the intracellular expression pattern of WT or mutant channels (S481L $Ca_v\beta_{2b}$, or A39V and G490R $Ca_v1.2$) tagged with enhanced yellow fluorescent protein (EYFP) (FIG. 4H-K). XYZ scans of WT and G490R channels revealed both a central and peripheral pattern of fluorescence, suggesting that a pool of these channels exists in intracellular organelles and that the proteins translocate normally to the cell membrane. In contrast, the fluorescence pattern of A39V channels was almost exclusively localized to intracellular organelles. The peripheral:central fluorescence ratio was similar for WT, G490R and S481 L (1.34±0.17, 1.58±0.31 and 0.94±0.1) (n=6), but much smaller for A39V (0.41±0.26) (p<0.05 compared to WT and G490R, n=6 cells), indicating that very few A39V channels were localized at the sarcolemma. Co-expression of WT and A39V channels was associated with more peripheral fluorescence (ratio=1.16±0.10) than A39V alone, indicating that the mutant channel does not interfere with trafficking of WT channels. Co-expression of WT and S481L $Ca_v\beta_{2b}$ channels yielded a ratio (1.04±0.10) similar to that of WT or S481L alone. These findings indicate that the loss of current observed with A39V is due to a defect in trafficking of mature $Ca_v1.2$ channels from the ER/Golgi complex to the cell membrane, whereas channels formed from G490R $Ca_v1.2$ or S481L $Ca_v\beta_{2b}$ subunits traffic normally.

The absence of an ST segment elevation in the two daughters of patient I may be explained on the basis of the well known low penetrance for clinical manifestation of the Brugada syndrome in young females. See, Antzelevitch et al., *Circulation*. 2005; 111:659-670. The apparently false positive response to ajmaline in III-7 has been reported previously in patients with Brugada syndrome. See, Hong et al., *J Cardiovasc Electrophysiol*. 2004; 15:64-69.

The present disclosure is the first to associate a cardiac calcium channel mutation with the Brugada syndrome or short QT intervals. Although the QTc intervals in the probands herein may be defined as "short" based on published reports, (Rautaharju et al., *Can J. Cardiol*. 1992; 8:690-

695; Viskin et al., *Heart Rhythm.* 2004; 1:587-591) they may not in all cases be considered as representing a Short QT syndrome, which thus far has been associated with QTc intervals ≦330 ms. Only one of the probands herein presented with a QTc≦330 ms (patient 1). It is noteworthy that Brugada syndrome is generally associated with a slight prolongation of the QT interval, particularly in the right precordial leads, presumably due to an accentuation of the action potential notch, which prolongs the action potential in right ventricular epicardium. Viskin et al., supra, reported that short QT intervals (QTc of ≦360 for males and ≦370 for females) are commonly observed in patients with idiopathic ventricular fibrillation (IVF). A less steep QT-RR relationship is also observed in these IVF patients, similar to the lack of rate dependence of QT reported in our patients. The slope of the QT/heart rate relation was −0.639 ms/bpm for patient 1 (III-6) and −0.869 ms/bpm for the symptomatic brother of patient 1 (III-5), −0.540 ms/bpm for patient 2, −0.991 ms/bpm for patient 3. These values are considerably less steep that those reported by Magnano et al., *J Am Coll Cardiol.* 2002; 39:1820-1826, for normal controls. (−1.37 ms/bpm). These distinctions are similar to those reported between SQT1 patients (−0.54 ms/bpm) and non-carrier controls (−1.29 ms/beats per minute (bpm). See, Wolpert et al., *J Cardiovasc Electrophysiol.* 2005; 16:54-58.

Quinidine has been proposed to be of therapeutic value in the Brugada syndrome (Antzelevitch et al., *Clinical Approaches to Tachyarrhythmias. The Brugada Syndrome.* Armonk, N.Y.: Futura Publishing Company, Inc.; 1999) as well as in the short QT syndrome. See, Gaita et al., *J Am Coll Cardiol.* 2004; 43:1494-1499. In the setting of Brugada syndrome, it is the $I_{to}$ blocking effect of the drug that is salutary, whereas in the short QT syndrome, it is the effect of the drug to block $I_{Kr}$ and $I_{Ks}$. Clinical evidence of the effectiveness of quinidine in inducible and spontaneous ventricular fibrillation (VF) was reported by Belhassen et al., *Circulation.* 2004; 110:1731-1737, in a prospective study of 25 Brugada syndrome patients. The ability of quinidine to prevent induction of VT and ventricular fibrillation (VF) and its effect to prolong QTc in patient 1 is consistent with these earlier reports.

Among 82 probands with a clinically robust diagnosis of Brugada syndrome in our registry, 6% (5) presented with a shorter than normal QT interval. Three of these five (60%) probands carried a calcium channel mutation, pointing to genetic heterogeneity for this phenotype. Fifteen percent of probands harbored a putative pathogenic mutation in SCN5A and 4.9% carried a mutation in calcium channel genes associated with Brugada syndrome and QT intervals >370 ms. The fraction of probands with SCN5A mutations (15%) is similar to that reported by Schulze-Bahr and co-workers (14%). See, Schulze-Bahr et al., *Hum Mutat.* 2003; 21:651-652. Whereas a gain of function in calcium channel current secondary to mutations in CACNA1C produces a sudden death syndrome associated with a prolongation of the QT interval (see, Splawski 1, supra and Splawski 11, supra), our findings indicate that a loss of function in calcium channel activity secondary to mutations in CACNA1C or CACNB2b can contribute to a sudden death syndrome consisting of a shorter than normal QT interval and ST segment elevation (Brugada syndrome phenotype). A similar mirror image of malignant syndromes has been demonstrated for a loss and gain of function in SCN5A (Brugada vs LQT3 syndromes) (Chen et al., *Nature.* 1998; 392:293-296; Wang et al., *Cell.* 1995; 80:805-811), KCNH2 (LQT2 vs. SQT1) (Brugada et al., *Circulation.* 2004; 109:30-35; Curran et al., *Cell.* 1995; 80:795-803), KCNQ1 (LQT1 vs. SQT2) (Bellocq et al., *Circulation.* 2004; 109:2394-2397 Wang et al. *Nat. Genet.* 1996; 12:17-23), and a loss and gain of function in KCNJ2 (Andersen-Tawil syndrome-LQT7 vs. SQT3) (Priori et al, supra).

It will be understood that various modifications may be made to the embodiments and examples disclosed herein. Therefore, the above description should not be construed as limiting, merely as exemplifications of preferred embodiments. Those skilled in the art may envision other modifications within the spirit and scope of the claims appended hereto.

---

What is claimed is:

1. A method of assessing a risk in a subject from shorter than normal QT interval and ST segment elevation which comprises screening said subject for a mutation in CACNB2 nucleic acid encoding wild-type CACNB2 polypeptide (SEQ. ID. NO: 2) by determining whether the CACNB2 nucleic acid or its expression products isolated from a sample of said subject codes for a polypeptide including a fragment having the amino acid sequence set forth in SEQ ID NO: 5, wherein the presence of said mutation in the sequence of the subject indicates a risk for shorter than normal QT interval and ST segment elevation syndrome.

2. The method of claim 1 wherein said expression product is mRNA of said CACNB2.

3. The method of claim 1 wherein one or more of the following procedures is carried out:
   (a) observing shifts in electrophoretic mobility of single-stranded DNA from said sample on non-denaturing polyacrylamide gels;
   (b) hybridizing a CACNB2 probe to genomic DNA isolated from said sample under conditions suitable for hybridization of said probe to said CACNB2;
   (c) determining hybridization of an allele-specific CACNB2 probe to genomic DNA from said sample;
   (d) amplifying all or part of said CACNB2 from said sample to produce an amplified sequence and sequencing the amplified sequence;
   (e) determining by nucleic acid amplification the presence of a specific CACNB2 mutant allele in said sample;
   (f) molecularly cloning all or part of said CACNB2 from said sample to produce a cloned sequence and sequencing the cloned sequence;
   (g) determining whether there is a mismatch between molecules (1) said CACNB2 genomic DNA or mRNA isolated from said sample, and (2) a nucleic acid probe complementary to the human wild-type CACNB2 nucleic acid, when molecules (1) and (2) are hybridized to each other to form a duplex;
   (h) amplification of said CACNB2 sequences in said sample and hybridization of the amplified sequences to nucleic acid probes which comprise wild-type gene sequences;
   (i) amplification of said CACNB2 sequences in said tissue and hybridization of the amplified sequences to nucleic acid probes which comprise said mutant CACNB2 sequences; or
   (j) determining in situ hybridization of said CACNB2 in said sample with one or more nucleic acid probes which comprise said CACNB2 sequence or a mutant sequence of said CACNB2.

4. The method of claim 1 wherein said sample is blood.

* * * * *

SEQUENCE LISTING

<160> NUMBER OF SEQ ID NOS: 7

<210> SEQ ID NO 1
<211> LENGTH: 2138
<212> TYPE: PRT
<213> ORGANISM: homo sapiens

<400> SEQUENCE: 1

Met Val Asn Glu Asn Thr Arg Met Tyr Ile Pro Glu Glu Asn His Gln
1               5                   10                  15

Gly Ser Asn Tyr Gly Ser Pro Arg Pro Ala His Ala Asn Met Asn Ala
            20                  25                  30

Asn Ala Ala Ala Gly Leu Ala Pro Glu His Ile Pro Thr Pro Gly Ala
        35                  40                  45

Ala Leu Ser Trp Gln Ala Ala Ile Asp Ala Ala Arg Gln Ala Lys Leu
    50                  55                  60

Met Gly Ser Ala Gly Asn Ala Thr Ile Ser Thr Val Ser Ser Thr Gln
65                  70                  75                  80

Arg Lys Arg Gln Gln Tyr Gly Lys Pro Lys Lys Gln Gly Ser Thr Thr
                85                  90                  95

Ala Thr Arg Pro Pro Arg Ala Leu Leu Cys Leu Thr Leu Lys Asn Pro
            100                 105                 110

```
Ile Arg Arg Ala Cys Ile Ser Ile Val Glu Trp Lys Ser Phe Glu Ile
    115                 120                 125

Ile Ile Leu Leu Thr Ile Phe Ala Asn Cys Val Ala Leu Ala Ile Tyr
130                 135                 140

Ile Pro Phe Pro Glu Asp Asp Ser Asn Ala Thr Asn Ser Asn Leu Glu
145                 150                 155                 160

Arg Val Glu Tyr Leu Phe Leu Ile Ile Phe Thr Val Glu Ala Phe Leu
                165                 170                 175

Lys Val Ile Ala Tyr Gly Leu Leu Phe His Pro Asn Ala Tyr Leu Arg
            180                 185                 190

Asn Gly Trp Asn Leu Leu Asp Phe Ile Ile Val Val Gly Leu Phe
        195                 200                 205

Ser Ala Ile Leu Glu Gln Ala Thr Lys Ala Asp Gly Ala Asn Ala Leu
    210                 215                 220

Gly Gly Lys Gly Ala Gly Phe Asp Val Lys Ala Leu Arg Ala Phe Arg
225                 230                 235                 240

Val Leu Arg Pro Leu Arg Leu Val Ser Gly Val Pro Ser Leu Gln Val
                245                 250                 255

Val Leu Asn Ser Ile Ile Lys Ala Met Val Pro Leu Leu His Ile Ala
            260                 265                 270

Leu Leu Val Leu Phe Val Ile Ile Tyr Ala Ile Ile Gly Leu Glu
        275                 280                 285

Leu Phe Met Gly Lys Met His Lys Thr Cys Tyr Asn Gln Glu Gly Ile
    290                 295                 300

Ala Asp Val Pro Ala Glu Asp Asp Pro Ser Pro Cys Ala Leu Glu Thr
305                 310                 315                 320

Gly His Gly Arg Gln Cys Gln Asn Gly Thr Val Cys Lys Pro Gly Trp
                325                 330                 335

Asp Gly Pro Lys His Gly Ile Thr Asn Phe Asp Asn Phe Ala Phe Ala
            340                 345                 350

Met Leu Thr Val Phe Gln Cys Ile Thr Met Glu Gly Trp Thr Asp Val
        355                 360                 365

Leu Tyr Trp Val Asn Asp Ala Val Gly Arg Asp Trp Pro Trp Ile Tyr
    370                 375                 380

Phe Val Thr Leu Ile Ile Ile Gly Ser Phe Phe Val Leu Asn Leu Val
385                 390                 395                 400

Leu Gly Val Leu Ser Gly Glu Phe Ser Lys Glu Arg Glu Lys Ala Lys
                405                 410                 415

Ala Arg Gly Asp Phe Gln Lys Leu Arg Glu Lys Gln Gln Leu Glu Glu
            420                 425                 430

Asp Leu Lys Gly Tyr Leu Asp Trp Ile Thr Gln Ala Glu Asp Ile Asp
        435                 440                 445

Pro Glu Asn Glu Asp Glu Gly Met Asp Glu Glu Lys Pro Arg Asn Met
    450                 455                 460

Ser Met Pro Thr Ser Glu Thr Glu Ser Val Asn Thr Glu Asn Val Ala
465                 470                 475                 480

Gly Gly Asp Ile Glu Gly Glu Asn Cys Gly Ala Arg Leu Ala His Arg
                485                 490                 495

Ile Ser Lys Ser Lys Phe Ser Arg Tyr Trp Arg Arg Trp Asn Arg Phe
            500                 505                 510

Cys Arg Arg Lys Cys Arg Ala Ala Val Lys Ser Asn Val Phe Tyr Trp
        515                 520                 525

Leu Val Ile Phe Leu Val Phe Leu Asn Thr Leu Thr Ile Ala Ser Glu
```

```
                530                 535                 540
His Tyr Asn Gln Pro Asn Trp Leu Thr Glu Val Gln Asp Thr Ala Asn
545                 550                 555                 560

Lys Ala Leu Leu Ala Leu Phe Thr Ala Glu Met Leu Leu Lys Met Tyr
                565                 570                 575

Ser Leu Gly Leu Gln Ala Tyr Phe Val Ser Leu Phe Asn Arg Phe Asp
                580                 585                 590

Cys Phe Val Val Cys Gly Gly Ile Leu Glu Thr Ile Leu Val Glu Thr
                595                 600                 605

Lys Ile Met Ser Pro Leu Gly Ile Ser Val Leu Arg Cys Val Arg Leu
610                 615                 620

Leu Arg Ile Phe Lys Ile Thr Arg Tyr Trp Asn Ser Leu Ser Asn Leu
625                 630                 635                 640

Val Ala Ser Leu Leu Asn Ser Val Arg Ser Ile Ala Ser Leu Leu Leu
                645                 650                 655

Leu Leu Phe Leu Phe Ile Ile Ile Phe Ser Leu Leu Gly Met Gln Leu
                660                 665                 670

Phe Gly Gly Lys Phe Asn Phe Asp Glu Met Gln Thr Arg Arg Ser Thr
                675                 680                 685

Phe Asp Asn Phe Pro Gln Ser Leu Leu Thr Val Phe Gln Ile Leu Thr
                690                 695                 700

Gly Glu Asp Trp Asn Ser Val Met Tyr Asp Gly Ile Met Ala Tyr Gly
705                 710                 715                 720

Gly Pro Ser Phe Pro Gly Met Leu Val Cys Ile Tyr Phe Ile Ile Leu
                725                 730                 735

Phe Ile Cys Gly Asn Tyr Ile Leu Leu Asn Val Phe Leu Ala Ile Ala
                740                 745                 750

Val Asp Asn Leu Ala Asp Ala Glu Ser Leu Thr Ser Ala Gln Lys Glu
                755                 760                 765

Glu Glu Glu Glu Lys Glu Arg Lys Lys Leu Ala Arg Thr Ala Ser Pro
                770                 775                 780

Glu Lys Lys Gln Glu Leu Val Glu Lys Pro Ala Val Gly Glu Ser Lys
785                 790                 795                 800

Glu Glu Lys Ile Glu Leu Lys Ser Ile Thr Ala Asp Gly Glu Ser Pro
                805                 810                 815

Pro Ala Thr Lys Ile Asn Met Asp Asp Leu Gln Pro Asn Glu Asn Glu
                820                 825                 830

Asp Lys Ser Pro Tyr Pro Asn Pro Glu Thr Thr Gly Glu Glu Asp Glu
                835                 840                 845

Glu Glu Pro Glu Met Pro Val Gly Pro Arg Pro Arg Pro Leu Ser Glu
850                 855                 860

Leu His Leu Lys Glu Lys Ala Val Pro Met Pro Glu Ala Ser Ala Phe
865                 870                 875                 880

Phe Ile Phe Ser Ser Asn Asn Arg Phe Arg Leu Gln Cys His Arg Ile
                885                 890                 895

Val Asn Asp Thr Ile Phe Thr Asn Leu Ile Leu Phe Phe Ile Leu Leu
                900                 905                 910

Ser Ser Ile Ser Leu Ala Ala Glu Asp Pro Val Gln His Thr Ser Phe
                915                 920                 925

Arg Asn His Ile Leu Phe Tyr Phe Asp Ile Val Phe Thr Thr Ile Phe
                930                 935                 940

Thr Ile Glu Ile Ala Leu Lys Met Thr Ala Tyr Gly Ala Phe Leu His
945                 950                 955                 960
```

```
Lys Gly Ser Phe Cys Arg Asn Tyr Phe Asn Ile Leu Asp Leu Leu Val
            965                 970                 975

Val Ser Val Ser Leu Ile Ser Phe Gly Ile Gln Ser Ser Ala Ile Asn
        980                 985                 990

Val Val Lys Ile Leu Arg Val Leu Arg Val Leu Arg Pro Leu Arg Ala
        995                 1000                1005

Ile Asn Arg Ala Lys Gly Leu Lys His Val Val Gln Cys Val Phe
    1010                1015                1020

Val Ala Ile Arg Thr Ile Gly Asn Ile Val Ile Val Thr Thr Leu
    1025                1030                1035

Leu Gln Phe Met Phe Ala Cys Ile Gly Val Gln Leu Phe Lys Gly
    1040                1045                1050

Lys Leu Tyr Thr Cys Ser Asp Ser Ser Lys Gln Thr Glu Ala Glu
    1055                1060                1065

Cys Lys Gly Asn Tyr Ile Thr Tyr Lys Asp Gly Glu Val Asp His
    1070                1075                1080

Pro Ile Ile Gln Pro Arg Ser Trp Glu Asn Ser Lys Phe Asp Phe
    1085                1090                1095

Asp Asn Val Leu Ala Ala Met Met Ala Leu Phe Thr Val Ser Thr
    1100                1105                1110

Phe Glu Gly Trp Pro Glu Leu Leu Tyr Arg Ser Ile Asp Ser His
    1115                1120                1125

Thr Glu Asp Lys Gly Pro Ile Tyr Asn Tyr Arg Val Glu Ile Ser
    1130                1135                1140

Ile Phe Phe Ile Ile Tyr Ile Ile Ile Ala Phe Phe Met Met
    1145                1150                1155

Asn Ile Phe Val Gly Phe Val Ile Val Thr Phe Gln Glu Gln Gly
    1160                1165                1170

Glu Gln Glu Tyr Lys Asn Cys Glu Leu Asp Lys Asn Gln Arg Gln
    1175                1180                1185

Cys Val Glu Tyr Ala Leu Lys Ala Arg Pro Leu Arg Arg Tyr Ile
    1190                1195                1200

Pro Lys Asn Gln His Gln Tyr Lys Val Trp Tyr Val Val Asn Ser
    1205                1210                1215

Thr Tyr Phe Glu Tyr Leu Met Phe Val Leu Ile Leu Leu Asn Thr
    1220                1225                1230

Ile Cys Leu Ala Met Gln His Tyr Gly Gln Ser Cys Leu Phe Lys
    1235                1240                1245

Ile Ala Met Asn Ile Leu Asn Met Leu Phe Thr Gly Leu Phe Thr
    1250                1255                1260

Val Glu Met Ile Leu Lys Leu Ile Ala Phe Lys Pro Lys His Tyr
    1265                1270                1275

Phe Cys Asp Ala Trp Asn Thr Phe Asp Ala Leu Ile Val Val Gly
    1280                1285                1290

Ser Ile Val Asp Ile Ala Ile Thr Glu Val Asn Pro Ala Glu His
    1295                1300                1305

Thr Gln Cys Ser Pro Ser Met Asn Ala Glu Glu Asn Ser Arg Ile
    1310                1315                1320

Ser Ile Thr Phe Phe Arg Leu Phe Arg Val Met Arg Leu Val Lys
    1325                1330                1335

Leu Leu Ser Arg Gly Glu Gly Ile Arg Thr Leu Leu Trp Thr Phe
    1340                1345                1350

Ile Lys Ser Phe Gln Ala Leu Pro Tyr Val Ala Leu Leu Ile Val
    1355                1360                1365
```

-continued

```
Met Leu Phe Phe Ile Tyr Ala   Val Ile Gly Met Gln    Val Phe Gly
    1370                1375                 1380

Lys Ile Ala Leu Asn Asp Thr   Thr Glu Ile Asn Arg    Asn Asn Asn
    1385                1390                 1395

Phe Gln Thr Phe Pro Gln Ala   Val Leu Leu Phe       Arg Cys Ala
    1400                1405                 1410

Thr Gly Glu Ala Trp Gln Asp   Ile Met Leu Ala Cys    Met Pro Gly
    1415                1420                 1425

Lys Lys Cys Ala Pro Glu Ser   Glu Pro Ser Asn Ser    Thr Glu Gly
    1430                1435                 1440

Glu Thr Pro Cys Gly Ser Ser   Phe Ala Val Phe Tyr    Phe Ile Ser
    1445                1450                 1455

Phe Tyr Met Leu Cys Ala Phe   Leu Ile Ile Asn Leu    Phe Val Ala
    1460                1465                 1470

Val Ile Met Asp Asn Phe Asp   Tyr Leu Thr Arg Asp    Trp Ser Ile
    1475                1480                 1485

Leu Gly Pro His His Leu Asp   Glu Phe Lys Arg Ile    Trp Ala Glu
    1490                1495                 1500

Tyr Asp Pro Glu Ala Lys Gly   Arg Ile Lys His Leu    Asp Val Val
    1505                1510                 1515

Thr Leu Leu Arg Arg Ile Gln   Pro Pro Leu Gly Phe    Gly Lys Leu
    1520                1525                 1530

Cys Pro His Arg Val Ala Cys   Lys Arg Leu Val Ser    Met Asn Met
    1535                1540                 1545

Pro Leu Asn Ser Asp Gly Thr   Val Met Phe Asn Ala    Thr Leu Phe
    1550                1555                 1560

Ala Leu Val Arg Thr Ala Leu   Arg Ile Lys Thr Glu    Gly Asn Leu
    1565                1570                 1575

Glu Gln Ala Asn Glu Glu Leu   Arg Ala Ile Ile Lys    Lys Ile Trp
    1580                1585                 1590

Lys Arg Thr Ser Met Lys Leu   Leu Asp Gln Val Val    Pro Pro Ala
    1595                1600                 1605

Gly Asp Asp Glu Val Thr Val   Gly Lys Phe Tyr Ala    Thr Phe Leu
    1610                1615                 1620

Ile Gln Glu Tyr Phe Arg Lys   Phe Lys Lys Arg Lys    Glu Gln Gly
    1625                1630                 1635

Leu Val Gly Lys Pro Ser Gln   Arg Asn Ala Leu Ser    Leu Gln Ala
    1640                1645                 1650

Gly Leu Arg Thr Leu His Asp   Ile Gly Pro Glu Ile    Arg Arg Ala
    1655                1660                 1665

Ile Ser Gly Asp Leu Thr Ala   Glu Glu Glu Leu Asp    Lys Ala Met
    1670                1675                 1680

Lys Glu Ala Val Ser Ala Ala   Ser Glu Asp Asp Ile    Phe Arg Arg
    1685                1690                 1695

Ala Gly Gly Leu Phe Gly Asn   His Val Ser Tyr Tyr    Gln Ser Asp
    1700                1705                 1710

Gly Arg Ser Ala Phe Pro Gln   Thr Phe Thr Thr Gln    Arg Pro Leu
    1715                1720                 1725

His Ile Asn Lys Ala Gly Ser   Ser Gln Gly Asp Thr    Glu Ser Pro
    1730                1735                 1740

Ser His Glu Lys Leu Val Asp   Ser Thr Phe Thr Pro    Ser Ser Tyr
    1745                1750                 1755

Ser Ser Thr Gly Ser Asn Ala   Asn Ile Asn Asn Ala    Asn Asn Thr
```

```
                    1760                1765                1770

Ala Leu Gly Arg Leu Pro Arg Pro Ala Gly Tyr Pro Ser Thr Val
    1775                1780                1785

Ser Thr Val Glu Gly His Gly Pro Pro Leu Ser Pro Ala Ile Arg
    1790                1795                1800

Val Gln Glu Val Ala Trp Lys Leu Ser Ser Asn Arg Cys His Ser
    1805                1810                1815

Arg Glu Ser Gln Ala Ala Met Ala Gly Gln Glu Glu Thr Ser Gln
    1820                1825                1830

Asp Glu Thr Tyr Glu Val Lys Met Asn His Asp Thr Glu Ala Cys
    1835                1840                1845

Ser Glu Pro Ser Leu Leu Ser Thr Glu Met Leu Ser Tyr Gln Asp
    1850                1855                1860

Asp Glu Asn Arg Gln Leu Thr Leu Pro Glu Glu Asp Lys Arg Asp
    1865                1870                1875

Ile Arg Gln Ser Pro Lys Arg Gly Phe Leu Arg Ser Ala Ser Leu
    1880                1885                1890

Gly Arg Arg Ala Ser Phe His Leu Glu Cys Leu Lys Arg Gln Lys
    1895                1900                1905

Asp Arg Gly Gly Asp Ile Ser Gln Lys Thr Val Leu Pro Leu His
    1910                1915                1920

Leu Val His His Gln Ala Leu Ala Val Ala Gly Leu Ser Pro Leu
    1925                1930                1935

Leu Gln Arg Ser His Ser Pro Ala Ser Phe Pro Arg Pro Phe Ala
    1940                1945                1950

Thr Pro Pro Ala Thr Pro Gly Ser Arg Gly Trp Pro Pro Gln Pro
    1955                1960                1965

Val Pro Thr Leu Arg Leu Glu Gly Val Glu Ser Ser Glu Lys Leu
    1970                1975                1980

Asn Ser Ser Phe Pro Ser Ile His Cys Gly Ser Trp Ala Glu Thr
    1985                1990                1995

Thr Pro Gly Gly Gly Gly Ser Ser Ala Ala Arg Arg Val Arg Pro
    2000                2005                2010

Val Ser Leu Met Val Pro Ser Gln Ala Gly Ala Pro Gly Arg Gln
    2015                2020                2025

Phe His Gly Ser Ala Ser Ser Leu Val Glu Ala Val Leu Ile Ser
    2030                2035                2040

Glu Gly Leu Gly Gln Phe Ala Gln Asp Pro Lys Phe Ile Glu Val
    2045                2050                2055

Thr Thr Gln Glu Leu Ala Asp Ala Cys Asp Met Thr Ile Glu Glu
    2060                2065                2070

Met Glu Ser Ala Ala Asp Asn Ile Leu Ser Gly Gly Ala Pro Gln
    2075                2080                2085

Ser Pro Asn Gly Ala Leu Leu Pro Phe Val Asn Cys Arg Asp Ala
    2090                2095                2100

Gly Gln Asp Arg Ala Gly Gly Glu Glu Asp Ala Gly Cys Val Arg
    2105                2110                2115

Ala Arg Gly Arg Pro Ser Glu Glu Glu Leu Gln Asp Ser Arg Val
    2120                2125                2130

Tyr Val Ser Ser Leu
    2135

<210> SEQ ID NO 2
<211> LENGTH: 606
```

```
<212> TYPE: PRT
<213> ORGANISM: Homo sapiens

<400> SEQUENCE: 2

Met Leu Asp Arg Arg Leu Ile Ala Pro Gln Thr Lys Tyr Ile Ile Pro
1               5                   10                  15

Gly Gly Ser Ala Asp Ser Tyr Thr Ser Arg Pro Ser Asp Ser Asp Val
            20                  25                  30

Ser Leu Glu Glu Asp Arg Glu Ala Val Arg Arg Glu Ala Glu Arg Gln
        35                  40                  45

Ala Gln Ala Gln Leu Glu Lys Ala Lys Thr Lys Pro Val Ala Phe Ala
    50                  55                  60

Val Arg Thr Asn Val Ser Tyr Ser Ala Ala His Glu Asp Asp Val Pro
65                  70                  75                  80

Val Pro Gly Met Ala Ile Ser Phe Glu Ala Lys Asp Phe Leu His Val
                85                  90                  95

Lys Glu Lys Phe Asn Asn Asp Trp Trp Ile Gly Arg Leu Val Lys Glu
            100                 105                 110

Gly Cys Glu Ile Gly Phe Ile Pro Ser Pro Val Lys Leu Glu Asn Met
        115                 120                 125

Arg Leu Gln His Glu Gln Arg Ala Lys Gln Gly Lys Phe Tyr Ser Ser
    130                 135                 140

Lys Ser Gly Gly Asn Ser Ser Ser Leu Gly Asp Ile Val Pro Ser
145                 150                 155                 160

Ser Arg Lys Ser Thr Pro Pro Ser Ser Ala Ile Asp Ile Asp Ala Thr
                165                 170                 175

Gly Leu Asp Ala Glu Glu Asn Asp Ile Pro Ala Asn His Arg Ser Pro
            180                 185                 190

Lys Pro Ser Ala Asn Ser Val Thr Ser Pro His Ser Lys Glu Lys Arg
        195                 200                 205

Met Pro Phe Phe Lys Lys Thr Glu His Thr Pro Pro Tyr Asp Val Val
    210                 215                 220

Pro Ser Met Arg Pro Val Val Leu Val Gly Pro Ser Leu Lys Gly Tyr
225                 230                 235                 240

Glu Val Thr Asp Met Met Gln Lys Ala Leu Phe Asp Phe Leu Lys His
                245                 250                 255

Arg Phe Glu Gly Arg Ile Ser Ile Thr Arg Val Thr Ala Asp Ile Ser
            260                 265                 270

Leu Ala Lys Arg Ser Val Leu Asn Asn Pro Ser Lys His Ala Ile Ile
        275                 280                 285

Glu Arg Ser Asn Thr Arg Ser Ser Leu Ala Glu Val Gln Ser Glu Ile
    290                 295                 300

Glu Arg Ile Phe Glu Leu Ala Arg Thr Leu Gln Leu Val Val Leu Asp
305                 310                 315                 320

Ala Asp Thr Ile Asn His Pro Ala Gln Leu Ser Lys Thr Ser Leu Ala
                325                 330                 335

Pro Ile Ile Val Tyr Val Lys Ile Ser Ser Pro Lys Val Leu Gln Arg
            340                 345                 350

Leu Ile Lys Ser Arg Gly Lys Ser Gln Ala Lys His Leu Asn Val Gln
        355                 360                 365

Met Val Ala Ala Asp Lys Leu Ala Gln Cys Pro Pro Glu Leu Phe Asp
    370                 375                 380

Val Ile Leu Asp Glu Asn Gln Leu Glu Asp Ala Cys Glu His Leu Ala
385                 390                 395                 400
```

-continued

```
Asp Tyr Leu Glu Ala Tyr Trp Lys Ala Thr His Pro Pro Ser Ser Ser
            405                 410                 415

Leu Pro Asn Pro Leu Leu Ser Arg Thr Leu Ala Thr Ser Ser Leu Pro
        420                 425                 430

Leu Ser Pro Thr Leu Ala Ser Asn Ser Gln Gly Ser Gln Gly Asp Gln
    435                 440                 445

Arg Thr Asp Arg Ser Ala Pro Ile Arg Ser Ala Ser Gln Ala Glu Glu
450                 455                 460

Glu Pro Ser Val Glu Pro Val Lys Lys Ser Gln His Arg Ser Ser Ser
465                 470                 475                 480

Ser Ala Pro His His Asn His Arg Ser Gly Thr Ser Arg Gly Leu Ser
                485                 490                 495

Arg Gln Glu Thr Phe Asp Ser Glu Thr Gln Glu Ser Arg Asp Ser Ala
            500                 505                 510

Tyr Val Glu Pro Lys Glu Asp Tyr Ser His Asp His Val Asp His Tyr
        515                 520                 525

Ala Ser His Arg Asp His Asn His Arg Asp Glu Thr His Gly Ser Ser
    530                 535                 540

Asp His Arg His Arg Glu Ser Arg His Ser Arg Asp Val Asp Arg
545                 550                 555                 560

Glu Gln Asp His Asn Glu Cys Asn Lys Gln Arg Ser Arg His Lys Ser
                565                 570                 575

Lys Asp Arg Tyr Cys Glu Lys Asp Gly Glu Val Ile Ser Lys Lys Arg
            580                 585                 590

Asn Glu Ala Gly Glu Trp Asn Arg Asp Val Tyr Ile Pro Gln
        595                 600                 605

<210> SEQ ID NO 3
<211> LENGTH: 11
<212> TYPE: PRT
<213> ORGANISM: Homo sapiens

<400> SEQUENCE: 3

Ala Ala Ala Gly Leu Val Pro Glu His Ile Pro
1               5                   10

<210> SEQ ID NO 4
<211> LENGTH: 11
<212> TYPE: PRT
<213> ORGANISM: Homo sapiens

<400> SEQUENCE: 4

Glu Gly Glu Asn Cys Arg Ala Arg Leu Ala His
1               5                   10

<210> SEQ ID NO 5
<211> LENGTH: 11
<212> TYPE: PRT
<213> ORGANISM: Homo sapiens

<400> SEQUENCE: 5

His Arg Ser Ser Ser Leu Ala Pro His His Asn
1               5                   10

<210> SEQ ID NO 6
<211> LENGTH: 6417
<212> TYPE: DNA
<213> ORGANISM: Homo sapiens

<400> SEQUENCE: 6
```

```
atggtcaatg agaatacgag gatgtacatt ccagaggaaa accaccaagg ttccaactat     60
gggagcccac gccccgccca tgccaacatg aatgccaatg cggcagcggg gctggcccct    120
gagcacatcc ccaccccggg ggctgccctg tcgtggcagg cggccatcga cgcagcccgg    180
caggctaagc tgatgggcag cgctggcaat gcgaccatct ccacagtcag ctccacgcag    240
cggaagcggc agcaatatgg gaaacccaag aagcagggca gcaccacggc cacacgcccg    300
ccccgagccc tgctctgcct gaccctgaag aaccccatcc ggagggcctg catcagcatt    360
gtcgaatgga aatcatttga aataattatt ttactgacta ttttttgccaa ttgtgtggcc    420 ttagcgatct atattcccttt tccagaagat gattccaacg ccaccaattc caacctggaa    480
cgagtggaat atctctttct cataattttt acggtggaag cgttttttaaa agtaatcgcc    540 tatggactcc tctttcaccc caatgcctac ctccgcaacg gctggaacct actagatttt    600
ataattgtgg ttgtggggct ttttagtgca attttagaac aagcaaccaa agcagatggg    660
gcaaacgctc tcggagggaa aggggccgga tttgatgtga aggcgctgag ggccttccgc    720
gtgctgcgcc ccctgcggct ggtgtccgga gtcccaagtc tccaggtggt cctgaattcc    780
atcatcaagg ccatggtccc cctgctgcac atcgccctgc ttgtgctgtt tgtcatcatc    840
atctacgcca tcatcggctt ggagctcttc atggggaaga tgcacaagac ctgctacaac    900
caggagggca tagcagatgt tccagcagaa gatgacccttt cccccttgtgc gctgaaacg    960 ggccacgggc ggcagtgcca gaacggcacg gtgtgcaagc ccggctggga tggtcccaag   1020
cacggcatca ccaactttga caactttgcc ttcgccatgc tcacggtgtt ccagtgcatc   1080
accatggagg gctggacgga cgtgctgtac tgggtcaatg atgccgtagg aagggactgg   1140
ccctggatct atttttgttac actaatcatc ataggggtcat ttttttgtact taacttggtt   1200 ctcggtgtgc ttagcggaga gttttccaaa gagagggaga aggccaaggc ccggggagat   1260
ttccagaagc tgcgggagaa gcagcagcta gaagaggatc tcaaaggcta cctggattgg   1320
atcactcagg ccgaagacat cgatcctgag aatgaggacg aaggcatgga tgaggagaag   1380
ccccgaaaca tgagcatgcc caccagtgag accgagtccg tcaacaccga aaacgtggct   1440
ggaggtgaca tcgagggaga aaactgcggg gccaggctgg cccaccggat ctccaagtca   1500
aagttcagcc gctactggcg ccggtggaat cggttctgca gaaggaagtg ccgcgccgca   1560
gtcaagtcta tgtcttcta ctggctggtg attttcctgg tgttcctcaa cacgctcacc   1620
attgcctctg agcactacaa ccagcccaac tggctcacag aagtccaaga cacggcaaac   1680
aaggccctgc tggcccctgtt cacggcagag atgctcctga gatgtacag cctgggcctg   1740 caggcctact tcgtgtccct cttcaaccgc tttgactgct tcgtcgtgtg tggcggcatc   1800
ctggagacca tcctggtgga gaccaagatc atgtccccac tgggcatctc cgtgctcaga   1860
tgcgtccggc tgctgaggat tttcaagatc acgaggtact ggaactcctt gagcaacctg   1920
gtggcatcct tgctgaactc tgtgcgctcc atcgcctccc tgctccttct cctcttcctc   1980
ttcatcatca tcttctccct cctggggatg cagctctttg gaggaaagtt caactttgat   2040
gagatgcaga cccggaggag cacattcgat aacttccccc agtccctcct cactgtgttt   2100
cagatcctga ccggggagga ctggaattcg gtgatgtatg atgggatcat ggcttatggc   2160
ggcccctctt ttccagggat gttagtctgt atttacttca tcatcctctt catctgtgga   2220
aactatatcc tactgaatgt gttcttggcc attgctgtgg acaacctggc tgatgctgag   2280
agcctcacat ctgcccaaaa ggaggaggaa gaggagaagg agagaaagaa gctgccaggg   2340
actgccagcc cagagaagaa acaagagttg gtggagaagc cggcagtggg ggaatccaag   2400
```

-continued

| | | | | | |
|---|---|---|---|---|---|
| gaggagaaga | ttgagctgaa | atccatcacg | gctgacggag | agtctccacc | cgccaccaag | 2460 |
| atcaacatgg | atgacctcca | gcccaatgaa | aatgaggata | agagccccta | ccccaaccca | 2520 |
| gaaactacag | gagaagagga | tgaggaggag | ccagagatgc | ctgtcggccc | tcgcccacga | 2580 |
| ccactctctg | agcttcacct | taaggaaaag | gcagtgccca | tgccagaagc | cagcgcgttt | 2640 |
| ttcatcttca | gctctaacaa | caggtttcgc | ctccagtgcc | accgcattgt | caatgacacg | 2700 |
| atcttcacca | acctgatcct | cttcttcatt | ctgctcagca | gcatttccct | ggctgctgag | 2760 |
| gacccggtcc | agcacacctc | cttcaggaac | catattctgt | tttattttga | tattgttttt | 2820 |
| accaccattt | tcaccattga | aattgctctg | aagatgactg | cttatgggggc | tttcttgcac | 2880 |
| aagggttctt | tctgccggaa | ctacttcaac | atcctggacc | tgctggtggt | cagcgtgtcc | 2940 |
| ctcatctcct | ttggcatcca | gtccagtgca | atcaatgtcg | tgaagatctt | gcgagtcctg | 3000 |
| cgagtactca | ggcccctgag | ggccatcaac | agggccaagg | ggctaaagca | tgtggttcag | 3060 |
| tgtgtgtttg | tcgccatccg | gaccatcggg | aacatcgtga | ttgtcaccac | cctgctgcag | 3120 |
| ttcatgtttg | cctgcatcgg | ggtccagctc | ttcaagggaa | agctgtacac | ctgttcagac | 3180 |
| agttccaagc | agacagaggc | ggaatgcaag | ggcaactaca | tcacgtacaa | agacggggag | 3240 |
| gttgaccacc | ccatcatcca | accccgcagc | tgggagaaca | gcaagtttga | ctttgacaat | 3300 |
| gttctggcag | ccatgatggc | cctcttcacc | gtctccacct | tcgaagggtg | gccagagctg | 3360 |
| ctgtaccgct | ccatcgactc | ccacacggaa | gacaagggcc | ccatctacaa | ctaccgtgtg | 3420 |
| gagatctcca | tcttcttcat | catctacatc | atcatcatcg | ccttcttcat | gatgaacatc | 3480 |
| ttcgtgggct | tcgtcatcgt | cacctttcag | gagcagggggg | agcaggagta | caagaactgt | 3540 |
| gagctggaca | agaaccagcg | acagtgcgtg | gaatacgccc | tcaaggcccg | gcccctgcgg | 3600 |
| aggtacatcc | ccaagaacca | gcaccagtac | aaagtgtggt | acgtggtcaa | ctccacctac | 3660 |
| ttcgagtacc | tgatgttcgt | cctcatcctg | ctcaacacca | tctgcctggc | catgcagcac | 3720 |
| tacggccaga | gctgcctgtt | caaaatcgcc | atgaacatcc | tcaacatgct | cttcactggc | 3780 |
| ctcttcaccg | tggagatgat | cctgaagctc | attgccttca | aacccaagca | ctatttctgt | 3840 |
| gatgcatgga | atacatttga | cgccttgatt | gttgtgggta | gcattgttga | tatagcaatc | 3900 |
| accgaggtaa | acccagctga | acatacccaa | tgctctccct | ctatgaacgc | agaggaaaac | 3960 |
| tcccgcatct | ccatcacctt | cttccgcctg | ttccgggtca | tgcgtctggt | gaagctgctg | 4020 |
| agccgtgggg | agggcatccg | gacgctgctg | tggaccttca | tcaagtcctt | ccaggccctg | 4080 |
| ccctatgtgg | ccctcctgat | cgtgatgctg | ttcttcatct | acgcggtgat | cgggatgcag | 4140 |
| gtgtttggga | aaattgccct | gaatgatacc | acagagatca | accggaacaa | caactttcag | 4200 |
| accttccccc | aggccgtgct | gctcctcttc | aggtgtgcca | ccggggaggc | ctggcaggac | 4260 |
| atcatgctgg | cctgcatgcc | aggcaagaag | tgtgcccag | agtccgagcc | cagcaacagc | 4320 |
| acggagggtg | aaacaccctg | tggtagcagc | tttgctgtct | tctacttcat | cagcttctac | 4380 |
| atgctctgtg | ccttcctgat | catcaacctc | tttgtagctg | tcatcatgga | caactttgac | 4440 |
| tacctgacaa | gggactggtc | catccttggt | ccccaccacc | tggatgagtt | taaaagaatc | 4500 |
| tgggcagagt | atgaccctga | agccaagggt | cgtatcaaac | acctggatgt | ggtgaccctc | 4560 |
| ctccggcgga | ttcagccgcc | actaggtttt | gggaagctgt | gccctcaccg | cgtggcttgc | 4620 |
| aaacgcctgg | tctccatgaa | catgcctctg | aacagcgacg | ggacagtcat | gttcaatgcc | 4680 |
| accctgtttg | ccctggtcag | gacggccctg | aggatcaaaa | cagaagggaa | cctagaacaa | 4740 |
| gccaatgagg | agctgcgggc | gatcatcaag | aagatctgga | agcggaccag | catgaagctg | 4800 |

```
ctggaccagg tggtgccccc tgcaggtgat gatgaggtca ccgttggcaa gttctacgcc    4860
acgttcctga tccaggagta cttccggaag ttcaagaagc gcaaagagca gggccttgtg    4920
ggcaagccct cccagaggaa cgcgctgtct ctgcaggctg gcttgcgcac actgcatgac    4980
atcgggcctg agatccgacg ggccatctct ggagatctca ccgctgagga ggagctggac    5040
aaggccatga aggaggctgt gtccgctgct tctgaagatg acatcttcag gagggccggt    5100
ggcctgttcg gcaaccacgt cagctactac caaagcgacg gccggagcgc cttccccag     5160
accttcacca ctcagcgccc gctgcacatc aacaaggcgg gcagcagcca gggcgacact    5220
gagtcgccat cccacgagaa gctggtggac tccaccttca ccccgagcag ctactcgtcc    5280
accggctcca acgccaacat caacaacgcc aacaacaccg ccctgggtcg cctccctcgc    5340
cccgccggct accccagcac ggtcagcact gtggagggcc acgggccccc cttgtcccct    5400
gccatccggg tgcaggaggt ggcgtggaag ctcagctcca acaggtgcca ctcccgggag    5460
agccaggcag ccatggcggg tcaggaggag acgtctcagg atgagaccta tgaagtgaag    5520
atgaaccatg acacggaggc ctgcagtgag cccagcctgc tctccacaga gatgctctcc    5580
taccaggatg acgaaaatcg caactgacg ctcccagagg aggacaagag ggacatccgg    5640
caatctccga gagggtttt cctccgctct gcctcactag gtcgaagggc ctccttccac    5700
ctggaatgtc tgaagcgaca gaaggaccga gggggagaca tctctcagaa gacagtcctg    5760
cccttgcatc tggttcatca tcaggcattg gcagtggcag gcctgagccc cctcctccag    5820
agaagccatt cccctgcctc attccctagg cctttgcca ccccaccagc cacacctggc    5880
agccgaggct ggcccccaca gcccgtcccc acctgcggc ttgaggggt cgagtccagt    5940
gagaaactca acagcagctt cccatccatc cactgcggct cctgggctga accaccccc    6000
ggtggcgggg gcagcagcgc cgcccggaga gtccggcccg tctccctcat ggtgcccagc    6060
caggctgggg ccccagggag gcagttccac ggcagtgcca gcagcctggt ggaagcggtc    6120
ttgatttcag aaggactggg gcagtttgct caagatccca agttcatcga ggtcaccacc    6180
caggagctgg ccgacgcctg cgacatgacc atagaggaga tggagagcgc ggccgacaac    6240
atcctcagcg ggggcgcccc acagagcccc aatggcgccc tcttacccctt tgtgaactgc    6300
agggacgcgg ggcaggaccg agccggggc gaagaggacg cgggctgtgt gcgcgcgcgg    6360
ggtcgaccga gtgaggagga gctccaggac agcagggtct acgtcagcag cctgtag      6417
```

<210> SEQ ID NO 7
<211> LENGTH: 1821
<212> TYPE: DNA
<213> ORGANISM: Homo sapiens

<400> SEQUENCE: 7

```
atgcttgaca gacgccttat agctcctcaa actaaataca ttattcctgg gggttcggca     60
gactcctaca ctagccgtcc atccgattcc gatgtatctc tggaggagga ccggaggca    120
gtgcgcagag aagcggagcg gcaggcccag gcacagttgg aaaaagcaaa gacaaagccc    180
gttgcatttg cggttcggac aaatgtcagc tacagtgcgg cccatgaaga tgatgttcca    240
gtgcctggca tggccatctc attcgaagca aaagattttc tgcatgttaa ggaaaaattt    300
aacaatgact ggtggatagg gcgattggta aagaaggct gtgaaatcgg attcattcca    360
agcccagtca aactagaaaa catgaggctg cagcatgaac agagagccaa gcaagggaaa    420
ttctactcca gtaaatcagg aggaaattca tcatccagtt tgggtgacat agtacctagt    480
tccagaaaat caacacctcc atcatctgct atagacatag atgctactgg cttagatgca    540
```

```
gaagaaaatg atattccagc aaaccaccgc tcccctaaac ccagtgcaaa cagtgtaacg      600
tcaccccact ccaaagagaa aagaatgccc ttctttaaga agacagagca cactcctccg      660
tatgatgtgg taccttccat gcgaccagtg gtcctagtgg gcccttctct gaagggctac      720
gaggtcacag atatgatgca aaaagcgctg tttgattttt taaaacacag atttgaaggg      780
cggatatcca tcacaagggt caccgctgac atctcgcttg ccaaacgctc ggtattaaac      840
aatcccagta agcacgcaat aatagaaaga tccaacacaa ggtcaagctt agcggaagtt      900
cagagtgaaa tcgaaaggat ttttgaactt gcaagaacat tgcagttggt ggtccttgac      960
gcggatacaa ttaatcatcc agctcaactc agtaaaacct ccttggcccc tattatagta     1020
tatgtaaaga tttcttctcc taaggtttta caaaggttaa taaaatctcg agggaaatct     1080
caagctaaac acctcaacgt ccagatggta gcagctgata aactggctca gtgtcctcca     1140
gagctgttcg atgtgatctt ggatgagaac cagcttgagg atgcctgtga gcaccttgcc     1200
gactatctgg aggcctactg gaaggccacc catcctccca gcagtagcct ccccaaccct     1260
ctccttagcc gtacattagc cacttcaagt ctgcctctta gccccaccct agcctctaat     1320
tcacagggtt ctcaaggtga tcagaggact gatcgctccg ctcctatccg ttctgcttcc     1380
caagctgaag aagaacctag tgtggaacca gtcaagaaat cccagcaccg ctcttcctcc     1440
tcagccccac accacaacca tcgcagtggg acaagtcgcg gcctctccag gcaagagaca     1500
tttgactcgg aaacccagga gagtcgagac tctgcctacg tagagccaaa ggaagattat     1560
tcccatgacc acgtggacca ctatgcctca caccgtgacc acaaccacag agacgagacc     1620
cacgggagca gtgaccacag acacagggag tcccggcacc gttcccggga cgtggatcga     1680
gagcaggacc acaacgagtg caacaagcag cgcagccgtc ataaatccaa ggatcgctac     1740
tgtgaaaagg atggagaagt gatatcaaaa aaacggaatg aggctgggga gtggaacagg     1800
gatgtttaca tcccccaatg a                                               1821
```